(12) United States Patent
Taniguchi

(10) Patent No.: US 9,649,090 B2
(45) Date of Patent: May 16, 2017

(54) ULTRASOUND DIAGNOSTIC IMAGING APPARATUS

(71) Applicant: KONICA MINOLTA, INC., Chiyoda-ku, Tokyo (JP)

(72) Inventor: Tetsuya Taniguchi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 400 days.

(21) Appl. No.: 14/218,675

(22) Filed: Mar. 18, 2014

(65) Prior Publication Data

US 2014/0288429 A1 Sep. 25, 2014

(30) Foreign Application Priority Data

Mar. 19, 2013 (JP) .................................. 2013-055837

(51) Int. Cl.
*A61B 8/14* (2006.01)
*G01S 7/52* (2006.01)
(Continued)

(52) U.S. Cl.
CPC .............. *A61B 8/14* (2013.01); *B06B 1/0215* (2013.01); *G01S 7/5202* (2013.01);
(Continued)

(58) Field of Classification Search
CPC ..... A61B 8/14; G01S 7/5202; G01S 7/52038; G01S 15/8963; B06B 1/0215; B06B 2201/76
See application file for complete search history.

(56) References Cited

U.S. PATENT DOCUMENTS 6,705,996 B2   3/2004   Kawagishi et al.
8,043,220 B2   10/2011  Okada et al.
(Continued)

FOREIGN PATENT DOCUMENTS

CN   1903132 A  *  1/2007   ............. B06B 1/064
CN   1909837 A     2/2007
(Continued)

OTHER PUBLICATIONS

Chinese Office Action (and English translation thereof) dated Jul. 31, 2015, issued in counterpart Chinese Application No. 201410100423.0.
(Continued)

*Primary Examiner* — Bo J Peng
(74) *Attorney, Agent, or Firm* — Holtz, Holtz & Volek PC

(57) ABSTRACT

Disclosed is an ultrasound diagnostic imaging apparatus including an ultrasound probe which outputs transmission ultrasound toward a subject due to a pulse signal being input and which outputs a received signal by receiving reflected ultrasound from the subject and a transmission unit which makes the ultrasound probe generate the transmission ultrasound by outputting a pulse signal whose drive waveform is formed of rectangular waves. The transmission unit outputs pulse signals whose drive waveforms are asymmetric to each other on a same scanning line for a plurality of times with a time interval therebetween. The ultrasound diagnostic imaging apparatus further includes an image generation unit which combines received signals each of which obtained from the reflected ultrasound of the transmission ultrasound generated by each output of pulse signal and generates ultrasound image data on a basis of a composite received signal.

9 Claims, 23 Drawing Sheets

(51) Int. Cl.
  *G01S 15/89* (2006.01)
  *B06B 1/02* (2006.01)

(52) U.S. Cl.
  CPC ...... *G01S 7/52038* (2013.01); *G01S 15/8963* (2013.01); *B06B 2201/76* (2013.01)

(56) References Cited

U.S. PATENT DOCUMENTS

| | | |
|---|---|---|
| 2004/0230121 A1 | 11/2004 | Hansen et al. |
| 2004/0254459 A1 | 12/2004 | Kristoffersen et al. |
| 2006/0058661 A1* | 3/2006 | Hirama ............... A61B 8/14 600/437 |
| 2007/0038082 A1 | 2/2007 | Mo et al. |
| 2008/0228076 A1 | 9/2008 | Azuma et al. |
| 2012/0310091 A1* | 12/2012 | Ohnuma ............... G01S 7/5202 600/443 |
| 2013/0137978 A1* | 5/2013 | Lee ................... G01S 7/5202 600/437 |

FOREIGN PATENT DOCUMENTS

| | | | |
|---|---|---|---|
| CN | 101642378 A * | 2/2010 | ............... A61B 8/00 |
| EP | 1726261 A1 | 11/2006 | |
| JP | 2000-300554 A | 10/2000 | |
| JP | 2000300554 A | 10/2000 | |
| JP | 2002-301068 A | 10/2002 | |
| JP | 2003-310609 A | 11/2003 | |

OTHER PUBLICATIONS

Japanese Office Action (and English translation thereof) dated Aug. 20, 2015, issued in counterpart Japanese Application No. 2013-055837.
Extended European Search Report dated Oct. 22, 2014, issued in counterpart European Application No. 14160189.8.
Chinese Office Action (and English translation thereof) dated Mar. 16, 2016, issued in counterpart Chinese Application No. 201410100423.0.

* cited by examiner

ULTRASOUND DIAGNOSTIC IMAGING APPARATUS

BACKGROUND OF THE INVENTION

1. Field of the Invention

The present invention relates to an ultrasound diagnostic imaging apparatus.

2. Description of Related Art

In ultrasound diagnosis, beating of a heart and movement of a fetus can be displayed in real time by a simple operation such as applying an ultrasound probe on body surface. Since ultrasound diagnosis is a highly safe procedure, ultrasound examination can be performed repeatedly.

In such technique for displaying an ultrasound image, it is known that an image with good contrast can be obtained by visualizing harmonic components (for example, frequencies $2f_0$, $3f_0$, etc.) of fundamental wave components (frequency $f_0$) of transmission signals. Such image capturing method is referred to as Tissue Harmonic Imaging.

Above mentioned harmonic components occur due to non-linear distortions that mainly occur when ultrasound transmits inside a subject. In other words, with respect to ultrasound which is emitted inside a living body, their signals deform while being transmitted through tissues due to their non-linear responses and the harmonic components increase. As a result, the corresponding received signals include frequency components $2f_0$ which are double the fundamental wave $f_0$ and frequency components $3f_0$ which are triple the fundamental wave $f_0$, for example.

Pulse inversion is known as a method to extract harmonic components in the tissue harmonic imaging. In the pulse inversion, the first and the second transmission pulse signals, one transmission pulse signal being a signal whose polarity or time is inverse of the other transmission pulse signal. Then, their received signals are combined to cancel out the fundamental wave components and emphasize the second harmonic components. Such technique is disclosed in JP 2000-300554, JP 2002-301068 and JP 2003-310609, for example.

SUMMARY OF THE INVENTION

In pulse inversion, fundamental wave components are required to be diminished sufficiently in order to obtain an ultrasound image of high image quality. In order to realize this, high positive and negative drive symmetry is required. However, in the techniques disclosed in JP 2000-300554, JP 2002-301068 and JP 2003-310609, a highly accurate and expensive transmission drive device is needed to output pulse signals which fulfill such high level of positive and negative drive symmetry. Therefore, such expensive transmission drive device cannot be used in a small size and low cost ultrasound diagnostic imaging apparatus and compromises had to be made in terms of image quality such as resolution and penetration.

The present invention was made in view of the above circumstances and an object of the present invention is to provide an ultrasound diagnostic imaging apparatus which can improve in penetration while maintaining resolution without having a transmission drive device that realizes high positive and negative drive symmetry.

In order to realize at least one object, an ultrasound diagnostic imaging apparatus reflecting one aspect of the present invention includes an ultrasound probe which outputs transmission ultrasound toward a subject due to a pulse signal being input and which outputs a received signal by receiving reflected ultrasound from the subject, and a transmission unit which makes the ultrasound probe generate the transmission ultrasound by outputting a pulse signal whose drive waveform is formed of rectangular waves, and the transmission unit outputs pulse signals whose drive waveforms are asymmetric to each other on a same scanning line for a plurality of times with a time interval therebetween, and the ultrasound diagnostic imaging apparatus further includes an image generation unit which combines received signals each of which obtained from the reflected ultrasound of the transmission ultrasound generated by each output of pulse signal and generates ultrasound image data on a basis of a composite received signal.

Preferably, the transmission unit outputs a first pulse signal and a second pulse signal, the second pulse being formed by changing at least one duty among a plurality of duties in the first pulse signal and performing time reversal or polarity reversal thereto.

Preferably, the transmission unit changes drive pulse duration of the plurality of pulse signals.

Preferably, the transmission unit outputs a first pulse signal and a second pulse signal whose drive pulse duration is different from drive pulse duration of the first pulse signal, the second pulse signal being formed by making a first duty among a plurality of duties in the first pulse signal be longer for a predetermined time period and performing time reversal or polarity reversal thereto.

Preferably, the transmission unit outputs the plurality of pulse signals so that a correlation coefficient of frequency components of the plurality of pulse signals be 0.85 or greater and less than 1 in a transmission and reception bandwidth at −20 dB of the ultrasound probe.

Preferably, in the ultrasound probe, a fractional bandwidth at −20 dB is 110% or greater.

Preferably, the pulse signal is formed of rectangular waves of five values or less.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Figure 1:
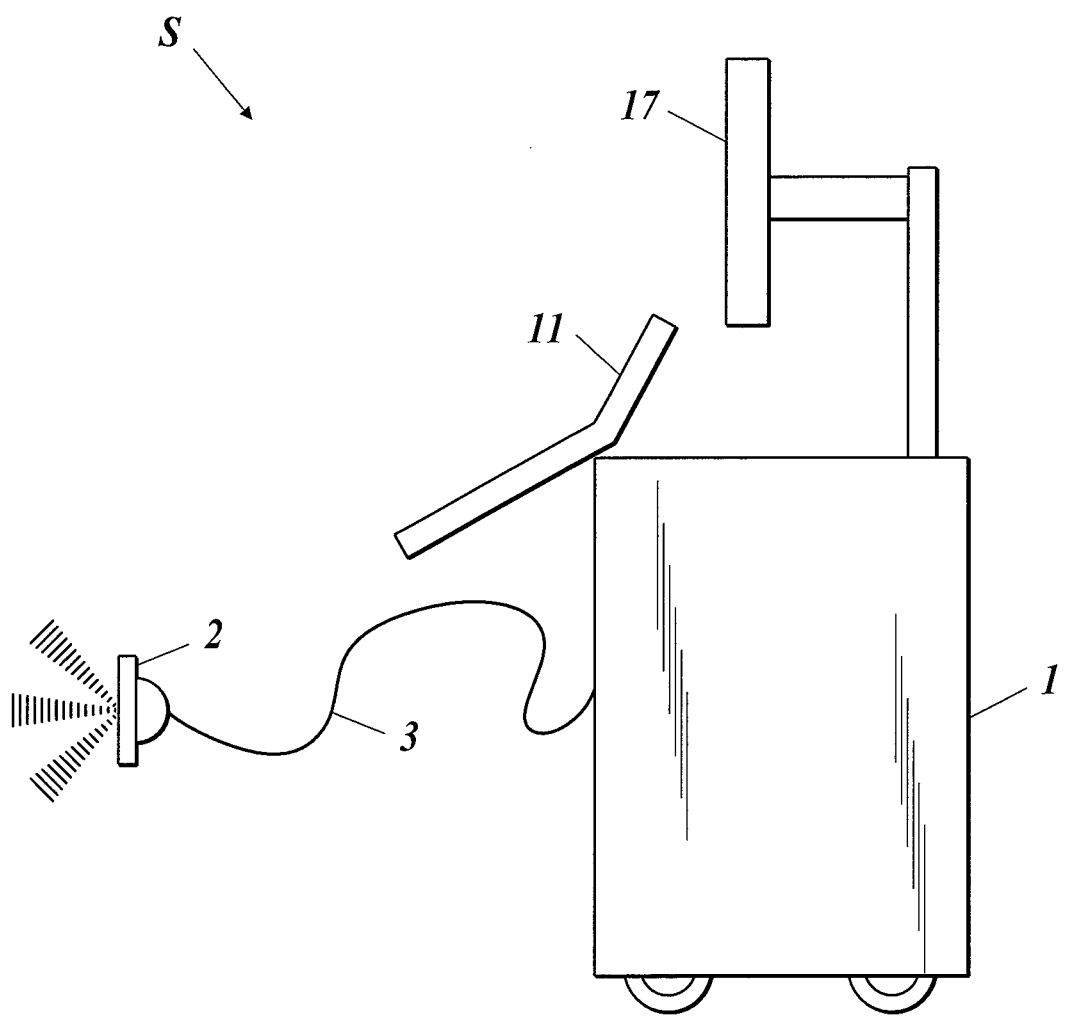
FIG. 1 is a drawing showing an outer structure of an ultrasound diagnostic imaging apparatus.

Hereinafter, the ultrasound diagnostic imaging apparatus according to an embodiment of the present invention will be described with reference to the drawings. However, the scope of the invention is not limited to the examples shown in the drawings. In the following description, same numeral references are used for similar functions and similar configurations and their descriptions are omitted.

Figure 2:
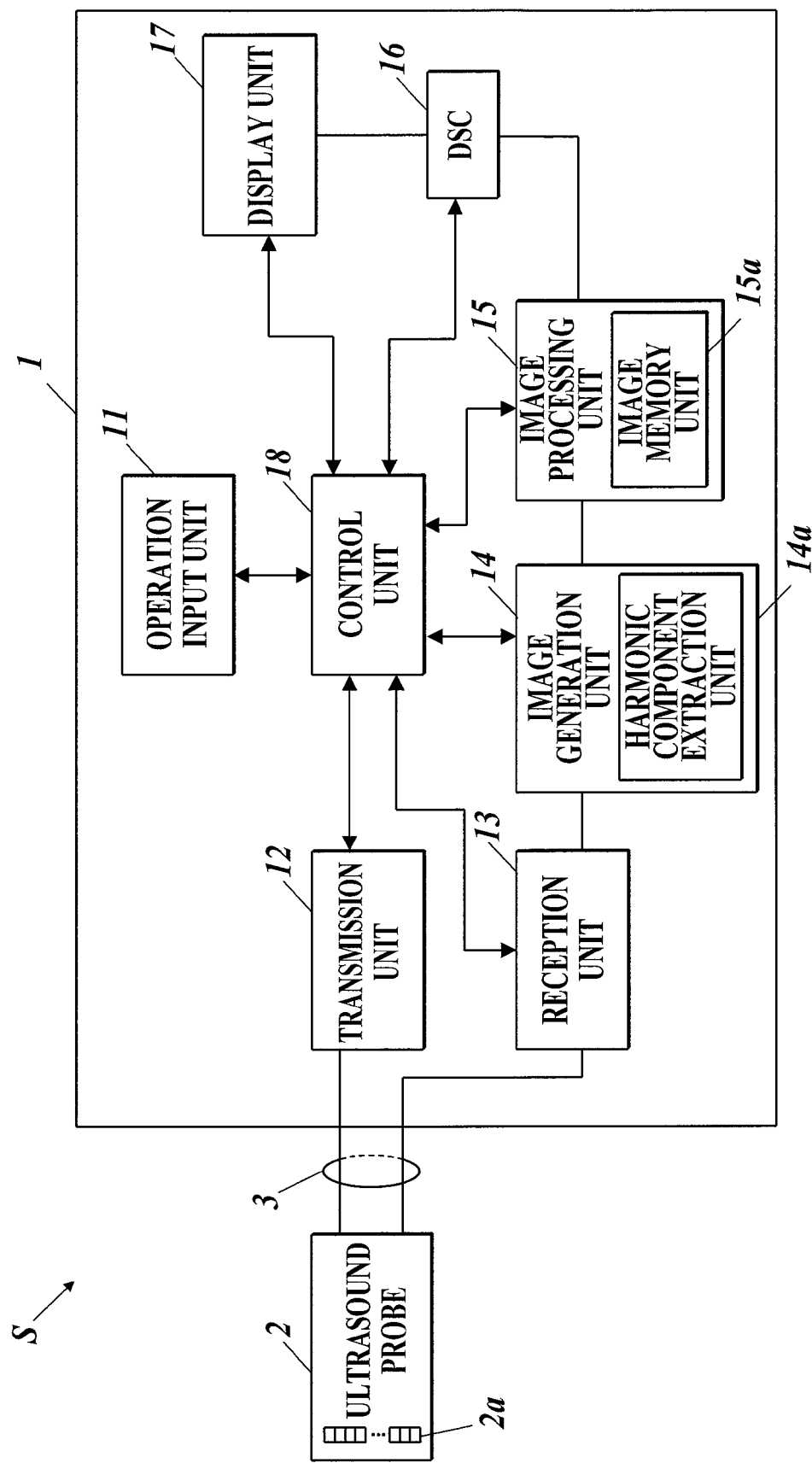
FIG. 2 is a block diagram showing a schematic configuration of the ultrasound diagnostic imaging apparatus.

As shown in FIGS. 1 and 2, the ultrasound diagnostic imaging apparatus S according to an embodiment includes an ultrasound diagnostic imaging apparatus main body 1 and an ultrasound probe 2. The ultrasound probe 2 transmits ultrasound (transmission ultrasound) to a subject such as a living body (not shown in the drawing) and receives reflected wave (reflected ultrasound: echo) of the ultrasound reflected off the subject. The ultrasound diagnostic imaging apparatus main body 1 is connected with the ultrasound probe 2 via a cable 3. The ultrasound diagnostic imaging apparatus main body 1 transmits drive signals which are electric signals to the ultrasound probe 2 to make the ultrasound probe 2 transmit transmission ultrasound to a subject and visualizes the inside state of the subject as an ultrasound image on the basis of the received signals which are electric signals generated in the ultrasound probe 2 according to the reflected ultrasound from inside of the subject received by the ultrasound probe 2.

The ultrasound probe 2 includes transducers 2a formed of piezoelectric elements and for example, the transducers 2a are aligned in a one-dimensional array in an orientation direction. In the embodiment, for example, an ultrasound probe 2 provided with 192 transducers 2a is used. Here, the transducers 2a may be aligned in a two-dimensional array. Further, the number of transducers 2a can be set arbitrarily. Although a linear scanning type electronic-scanning probe is used as the ultrasound probe 2 in the embodiment, either an electronic-scanning type or a mechanic-scanning type can be used. Further, any type of linear scanning, sector scanning and convex scanning can be adopted. In the embodiment, the transmission ultrasound having high resolution can be efficiently obtained by using an ultrasound probe which can transmit ultrasound in a broad band with good sensitivity, and an even better ultrasound image can be obtained. The bandwidth of the ultrasound probe can be set arbitrarily; however, it is preferred that the fractional bandwidth at −20 dB is 110% or greater.

As shown in FIG. 2, the ultrasound diagnostic imaging apparatus main body 1 includes an operation input unit 11, a transmission unit 12, a reception unit 13, an image generation unit 14, an image processing unit 15, a DSC (Digital Scan Converter) 16, a display unit 17 and a control unit 18, for example.

The operation input unit 11 includes various types of switches, buttons, a track ball, a mouse, a key board and the like for inputting commands for instructing the start of diagnosis and data such as personal information relating to a subject, etc. and the operation input unit 11 outputs operation signals to the control unit 18.

Figure 3:
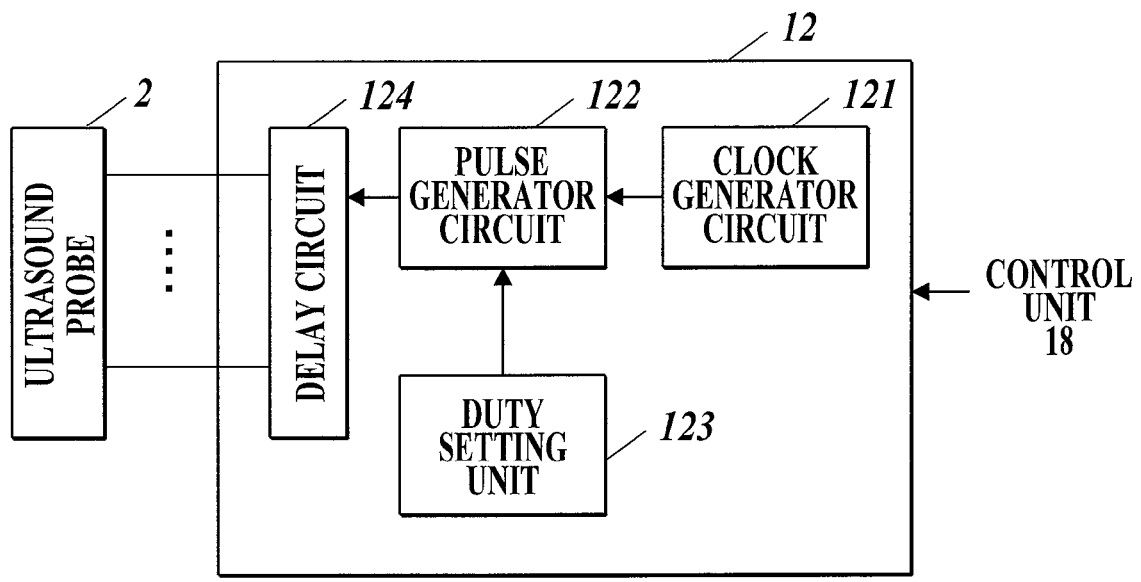
FIG. 3 is a block diagram showing a schematic configuration of a transmission unit.

The transmission unit 12 is a circuit for supplying drive signals which are electric signals to the ultrasound probe 2 via the cable 3 according to the control of the control unit 18 to make the ultrasound probe 2 generate transmission ultrasound. More specifically, as shown in FIG. 3, the transmission unit 12 includes a clock generator circuit 121, a pulse generator circuit 122, a duty setting unit 123 and a delay circuit 124, for example.

The clock generator circuit 121 is a circuit for generating a clock signal for deciding the transmission timing and the transmission frequency of a drive signal.

Figure 4:
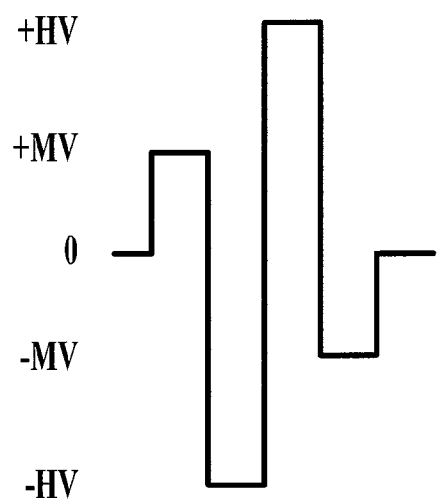
FIG. 4 is a drawing for explaining a drive waveform of a pulse signal.

The pulse generator circuit 122 is a circuit for generating a pulse signal as a drive signal in a predetermined cycle. The pulse generator circuit 122 can generate a pulse signal of rectangular waves by switching between 5 values of voltage (+HV/+MV/0/−MV/−HV) and output the voltage as shown in FIG. 4, for example. Here, the amplitude of the pulse signal is made so as to be the same in the positive polarity and in the negative polarity. However, this is not limitative in any way. In the embodiment, a pulse signal is output by switching among five voltage values. However, the voltage values are not limited to five values and can be set to arbitrary number of values, although, the number of values is desired to be five values or less. In such way, the degree of freedom for controlling the frequency components can be improved at a low cost and transmission ultrasound having even higher resolution can be obtained.

The duty setting unit 123 sets the duty ratio of a pulse signal which is output from the pulse generator circuit 122. That is, the pulse generator circuit 122 outputs a pulse signal of a pulse waveform according to the duty ratio set by the duty setting unit 123. The duty ratio can be changed by the input operation performed on the operation input unit 11.

The delay circuit 124 is a circuit for setting delay times in transmission timings of drive signals for individual paths corresponding to the transducers and delays the transmission of the drive signals for the set delay times to concentrate the transmission beams constituted of transmission ultrasound.

The transmission unit 12 configured as described above sequentially switches the transducer 2a which supplies a drive signal among the plurality of transducers 2a by a predetermined number of transducers 2a for every transmission and reception of ultrasound according to the control of the control unit 18 and supplies drive signals to the selected plurality of transducers 2a to perform scanning.

In the embodiment, pulse inversion can be performed in order to extract the after-mentioned harmonic components. That is, when performing pulse inversion, the transmission unit 12 can transmit the first pulse signal and the second pulse signal whose polarity is inverse of that of the first pulse signal on the same scanning line with a time interval therebetween. At this time, the second pulse signal formed by changing at least one of the plurality of duties of the first pulse signal so as to be time reversed, the second pulse signal having a waveform asymmetric to that of the first pulse signal, may be transmitted. Here, asymmetric waveform means that waveforms are not line-symmetric nor point-symmetric to each other. In other words, a waveform of a pulse signal does not match the time reversed waveform nor the polarity reversed waveform of the pulse signal (not symmetric). Further, the second pulse signal may be a signal formed by performing polarity reversal on the first pulse signal. The number of times a pulse signal is to be output when performing pulse inversion is not limited to two times and may be three times or more.

The reception unit 13 is a circuit for receiving received signals which are electric signals from the ultrasound probe 2 via the cable 3 in compliance with the control of the control unit 18. The reception unit 13 is provided with an amplifier, an A/D conversion circuit and a phasing addition circuit, for example. The amplifier is a circuit for amplifying the received signals at a preset amplification factor for the individual paths corresponding to the transducers 2a. The A/D conversion circuit is a circuit for performing analog/digital conversion (A/D conversion) on the amplified received signals. The phasing addition circuit is a circuit for adjusting time phases of the received signals to which A/D conversion is performed by applying the delay times to the individual paths respectively corresponding to the transducers 2a and generating sound ray data by adding the adjusted received signals (phase addition).

The image generation unit 14 generates B-mode image data by performing envelope detection, logarithmic amplification and the like on the sound ray data from the reception unit 13 and performing brightness conversion by performing gain adjustment and the like. In other words, B-mode image data is data where intensities of received signals are expressed in terms of brightness. The B-mode image data which is generated in the image generation unit 14 is transmitted to the image processing unit 15. Further, the image generation unit 14 includes the harmonic component extraction unit 14a.

The harmonic component extraction unit 14a performs pulse inversion and extracts harmonic components from the received signals which are output from the reception unit 13. In the embodiment, signal components mainly constituted of second harmonic components can be extracted by the harmonic component extraction unit 14a. A second harmonic component can be extracted by filtering after adding (composition) the received signals obtained from the reflected ultrasounds corresponding to the two transmission ultrasounds respectively generated from the above mentioned first pulse signal and second pulse signal and removing the fundamental wave component included in the added received signal. However, in a so-called low-end ultrasound diagnostic imaging apparatus which is small and manufactured at low cost, a fundamental wave component cannot be removed completely even when the reflection ultrasound corresponding to the transmission ultrasound generated based on the first pulse signal and the reflection ultrasound corresponding to the transmission ultrasound generated based on the second pulse signal are combined and so-called remainder occurs. In the embodiment, by combining the reflection ultrasound corresponding to the transmission ultrasound generated based on the first pulse signal and the reflection ultrasound corresponding to the transmission ultrasound generated based on the second pulse signal which is asymmetric to the first pulse signal as described above, the remainder component is positively controlled and utilized in order to improve in penetration while maintaining resolution even in a low-end ultrasound diagnostic imaging apparatus.

The image processing unit 15 includes an image memory unit 15a constituted of a semiconductor memory such as a DRAM (Dynamic Random Access Memory). The image processing unit 15 stores B-mode image data output from the image generation unit 14 in the image memory unit 15a in frame units. The image data in frame units may be called ultrasound image data or frame image data. The image processing unit 15 arbitrarily reads out the ultrasound image data stored in the image memory unit 15a and outputs the ultrasound image data to the DSC 16.

The DSC 16 converts the ultrasound image data received by the image processing unit 15 into an image signal of television signal scan mode and outputs the image signal to the display unit 17.

As for the display unit 17, display apparatuses such as a LCD (Liquid Crystal Display), a CRT (Cathode-Ray Tube) display, an organic EL (Electronic Luminescence) display, an inorganic EL display or a plasma display can be applied. The display unit 17 displays an ultrasound image on the display screen according to the image signal output from the DSC 16.

The control unit 18 includes a CPU (Central Processing Unit), a ROM (Read Only Memory) and a RAM (Random Access Memory), for example. The control unit 18 reads out and opens various types of programs such as a system program stored in the ROM in the RAM and collectively controls the operations of the components in the ultrasound diagnostic imaging apparatus S in compliance with the opened programs.

The ROM is configured of a non-volatile memory of semiconductor or the like, and stores a system program corresponding to the ultrasound diagnostic imaging apparatus S, various types of processing programs which can be executed on the system program, various types of data and the like. These programs are stored in the forms of program codes which can be read by a computer and the CPU sequentially executes the operations according to the program codes.

The RAM forms a work area in which various types of programs to be executed by the CPU and data relating to these programs are to be stored temporarily.

Embodiment 1

Hereinafter, the present invention will be described in terms of embodiment examples. However, it is needless to say that the present invention is not limited to the embodiment examples.

In the following embodiment examples, as for the transmission unit 12, a transmission unit which transmits a drive signal of waveform No. 1 shown in FIG. 6 as the first pulse signal and a drive signal of waveform No. 15 shown in FIG. 20 having a polarity reverse of that of the first pulse signal and being symmetric to the first pulse signal as the second pulse signal and whose maximum voltage amplitude is 6.2Vpp as a result of adding the actual drive voltages actually observed at the end portion of the ultrasound probe and measured by an oscilloscope when the ultrasound probe is connected is used. Further, the transmission unit 12 can outputs drive signals by switching between five voltage values which are +44V (+HV), +22V (+MV), 0V, −22V (−MV) and −44V (−HV).

Since the drive waveforms shown in the embodiment examples are all drive signals as control signals, the waveforms are symmetric in the comparison examples 1 and 2. However, because a cheap transmission unit which does not realize sufficient symmetry as described above is used in the embodiment example, when the actual drive voltage waveforms observed at the end portion of the ultrasound probe are added, remainder occurs in reality even in the cases of Comparison examples 1 and 2.

Embodiment Example 1

Figure 5:
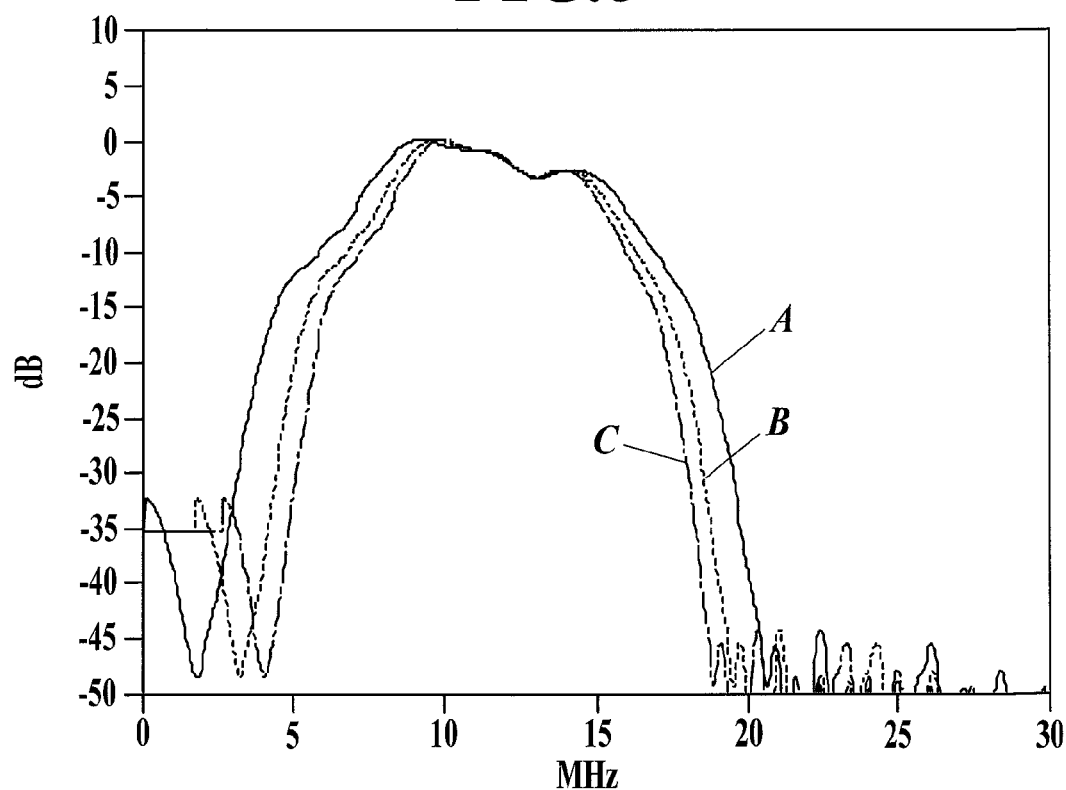
FIG. 5 is a drawing for explaining a transmission bandwidth of an ultrasound probe.

First, as the above described ultrasound probe 2, an ultrasound probe having the following characteristics is used, the characteristics being: the minimum frequency (FL20) at −20 dB in transmission is 3.8 MHz, the maximum frequency (FH20) at −20 dB in transmission is 18.6 MHz, the center frequency (FC20) is 11.2 MHz and the fractional bandwidth at −20 dB in transmission is 1320. This ultrasound probe is referred to as the ultrasound probe A. The line A in FIG. 5 shows the transmission bandwidth shape of the ultrasound probe A. In FIG. 5, the horizontal axis indicates frequency and the vertical axis indicates sensitivity.

Figure 8:
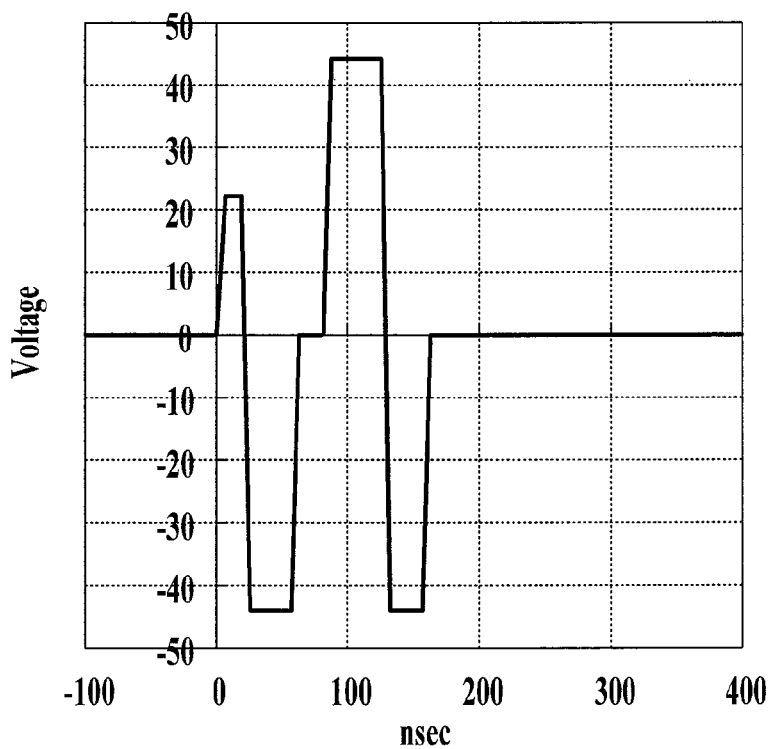
FIG. 8 is a drawing for explaining a drive waveform of a pulse signal, the drive waveform being referred to as waveform No. 3.

The first pulse signal output from the transmission unit 12 has the drive signal of waveform No. 3 as shown in FIG. 8. The drive signal of waveform No. 3 shows that the voltage starts increasing at 0 nec, reaches +MV at 7 nsec and maintains +MV until 19 nsec (the first duty). Thereafter, the voltage starts decreasing at 19 nsec, reaches −HV at 25 nsec and maintains −HV until 57 nsec (the second duty). Thereafter, the voltage starts increasing at 57 nsec, reaches 0V at 63 nsec and maintains 0V until 82 nsec (the third duty). Thereafter, the voltage starts increasing at 82 nsec, reaches +HV at 88 nsec and maintains +HV until 125 nsec (the fourth duty). Thereafter, the voltage starts decreasing at 125 nsec, reaches −HV at 132 nsec and maintains −HV until 157 nsec (the fifth duty). Thereafter, the voltage starts increasing at 157 nsec and reaches 0V at 163 nsec. In such way, the drive duration (drive pulse duration) of the drive signal of waveform No. 3 is 163 nsec.

Figure 14:
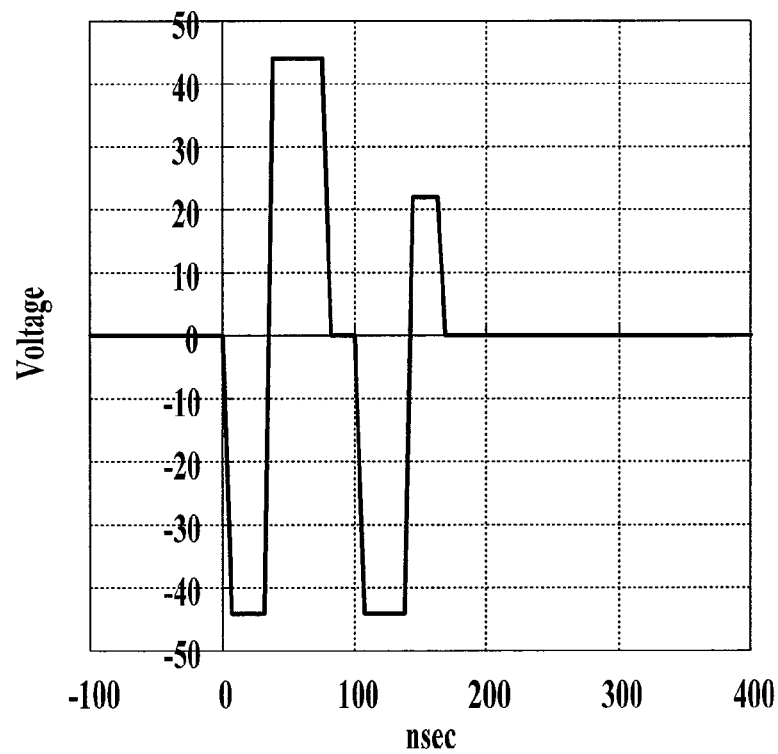
FIG. 14 is a drawing for explaining a drive waveform of a pulse signal, the drive waveform being referred to as waveform No. 9.
Figure 23A:
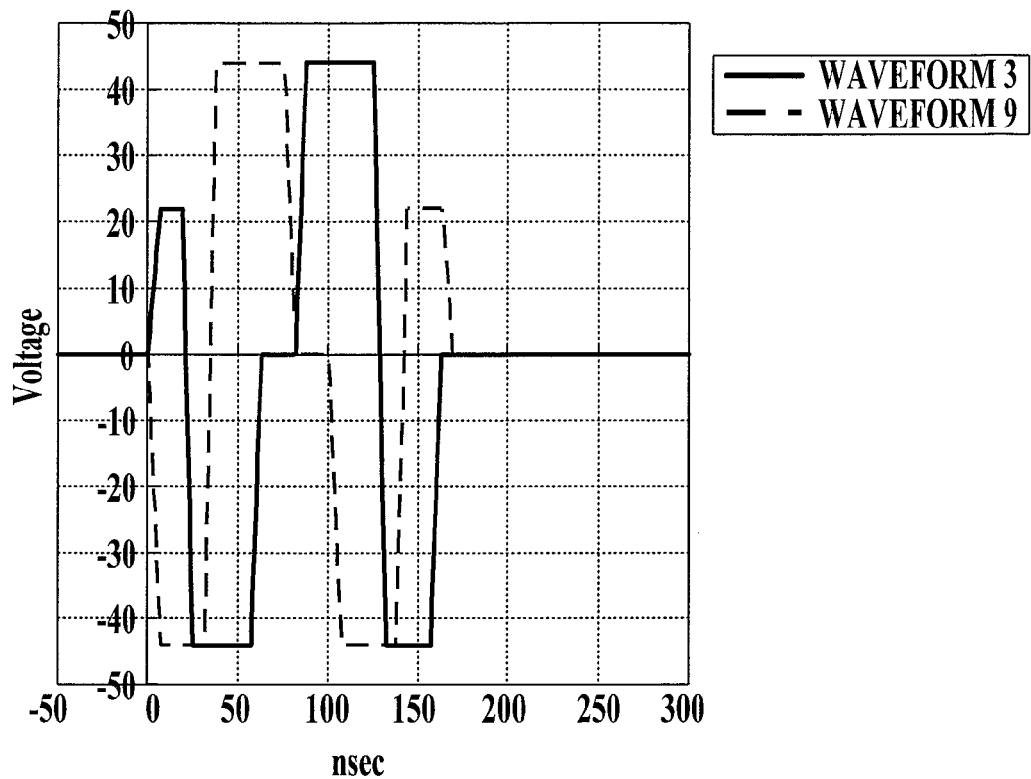
FIG. 23A is a drawing for explaining drive waveforms of pulse signals.
Figure 23B:
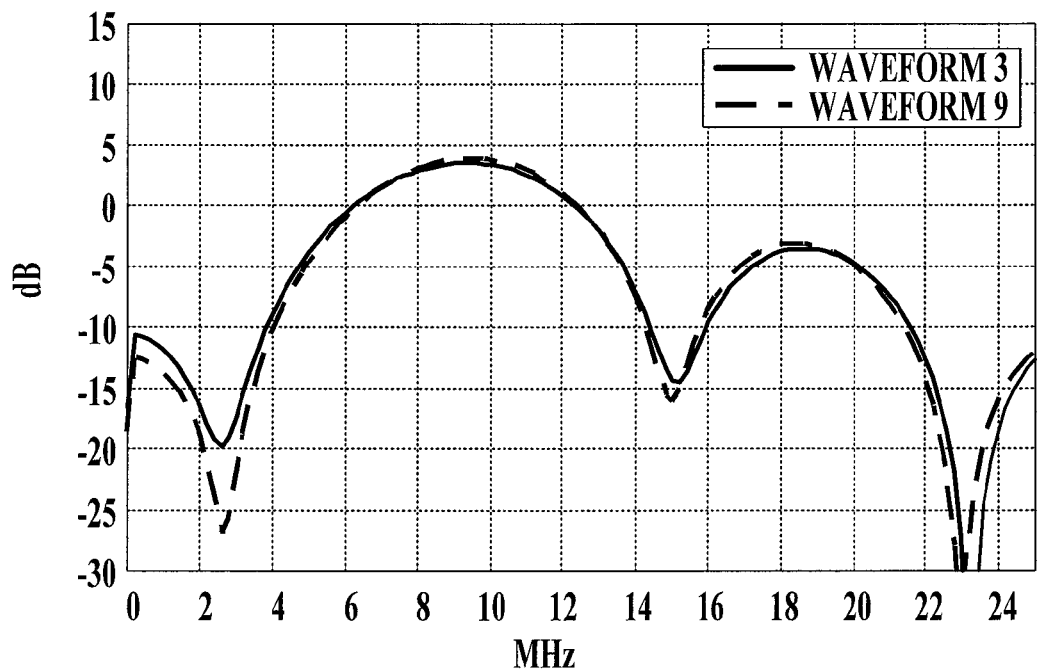
FIG. 23B is a drawing for explaining results of performing frequency analysis on the drive waveforms shown in FIG. 23A.

Further, the second pulse signal is a drive signal of waveform No. 9 as shown in FIG. 14. The drive signal of waveform No. 9 shows that the voltage starts decreasing at 0 nsec, reaches −HV at 7 nsec and maintains −HV until 32 nsec (the first duty). Thereafter, the voltage starts increasing at 32 nsec, reaches +HV at 38 nsec and maintains +HV until 75 nsec (the second duty). Thereafter, the voltage starts decreasing at 75 nsec, reaches 0V at 82 nsec and maintains 0V until 100 nsec (the third duty). Thereafter, the voltage starts decreasing at 100 nsec, reaches −HV at 107 nsec and maintains −HV until 138 nsec (the fourth duty). Thereafter, the voltage starts increasing at 138 nsec, reaches +MV at 144 nsec and maintains +MV until 163 nsec (the fifth duty). Thereafter, the voltage starts decreasing at 163 nsec and reaches 0V at 169 nsec. In such way, the drive duration of the drive signal of waveform No. 9 is 169 nsec, the drive duration being longer by 6 nsec comparing to the drive signal of waveform No. 3. Further, as shown in FIG. 23A, the drive signal of waveform No. 9 which is the second pulse signal has a waveform that is time symmetric to the waveform of the drive signal of waveform No. 3. (In the following embodiment examples, with respect to the duties in the first pulse signal and their corresponding duties in the second pulse signal, there may be differences about 1 nsec. However, such differences are within the margin of error and are permissible. In other words, such errors are permissible within the scope of the present invention.) However, comparing to the length of the first duty in the waveform No. 3, the length of the fifth duty in the waveform No. 9 corresponding to the first duty in the waveform No. 3 is longer by 7 nsec. The frequency power spectrums obtained by performing frequency analysis on these waveforms are shown in FIG. 23B. In FIG. 23A, the horizontal axis indicates time and the vertical axis indicates voltage. In FIG. 23B, the horizontal axis indicates frequency and the vertical axis indicates signal intensity. The correlation coefficient of these frequency power spectrums in the transmission frequency band (3.8 MHz-18.6 MHz) at −20 dB of the ultrasound probe A is 0.992.

Embodiment Example 2

First, as for the ultrasound probe 2, the ultrasound probe A same as that in Embodiment example 1 is used.

The first pulse signal output from the transmission unit 12 is a drive signal of waveform No. 3 same as that in Embodiment example 1.

Figure 9:
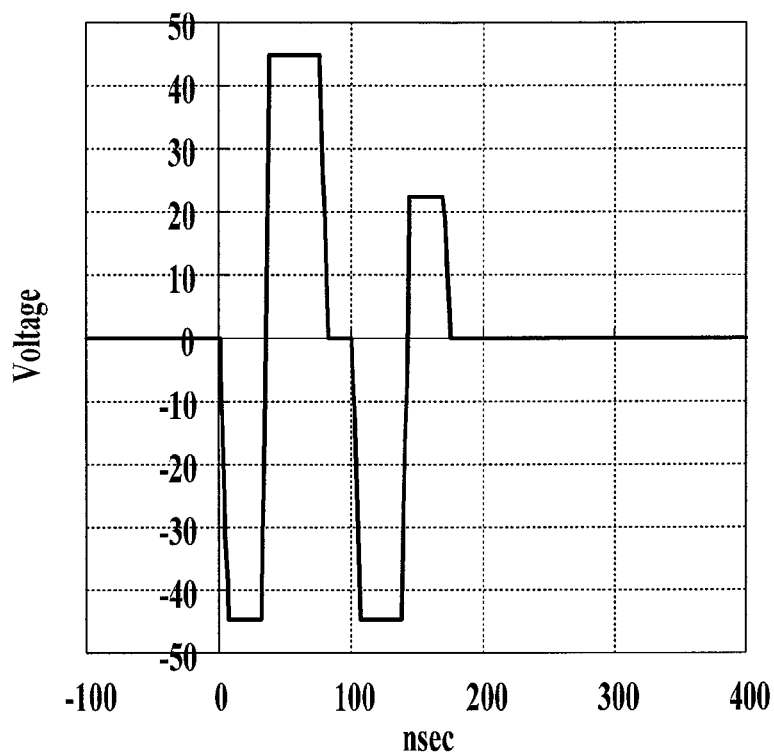
FIG. 9 is a drawing for explaining a drive waveform of a pulse signal, the drive waveform being referred to as waveform No. 4.
Figure 24A:
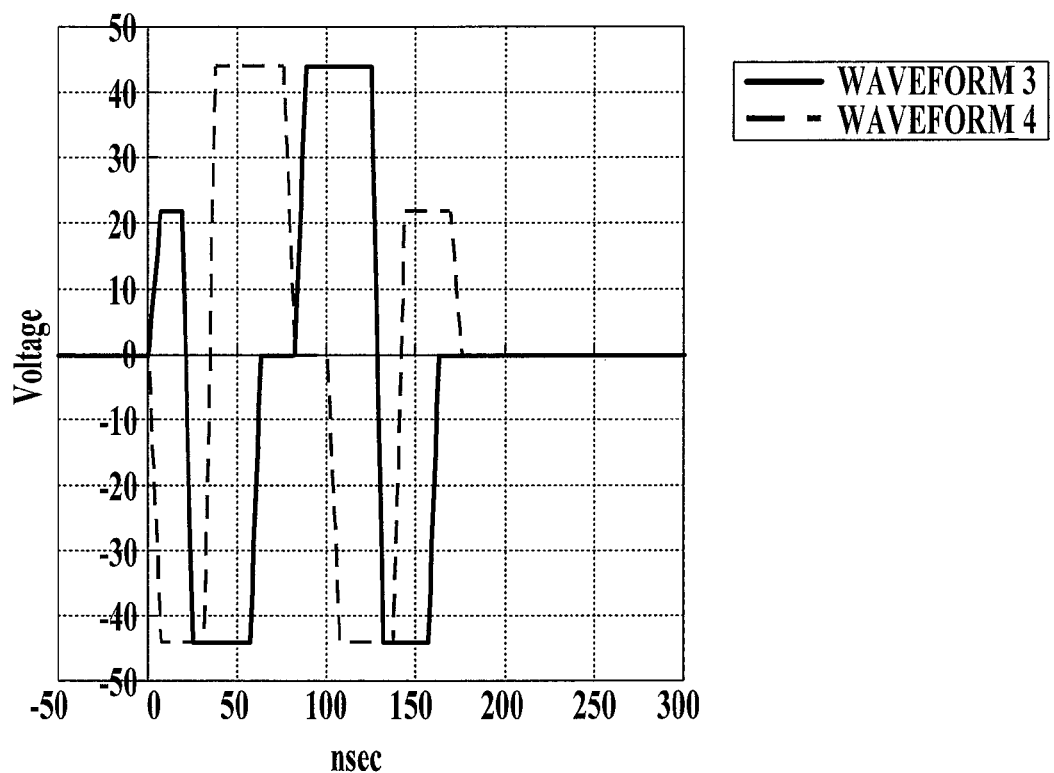
FIG. 24A is a drawing for explaining drive waveforms of pulse signals.
Figure 24B:
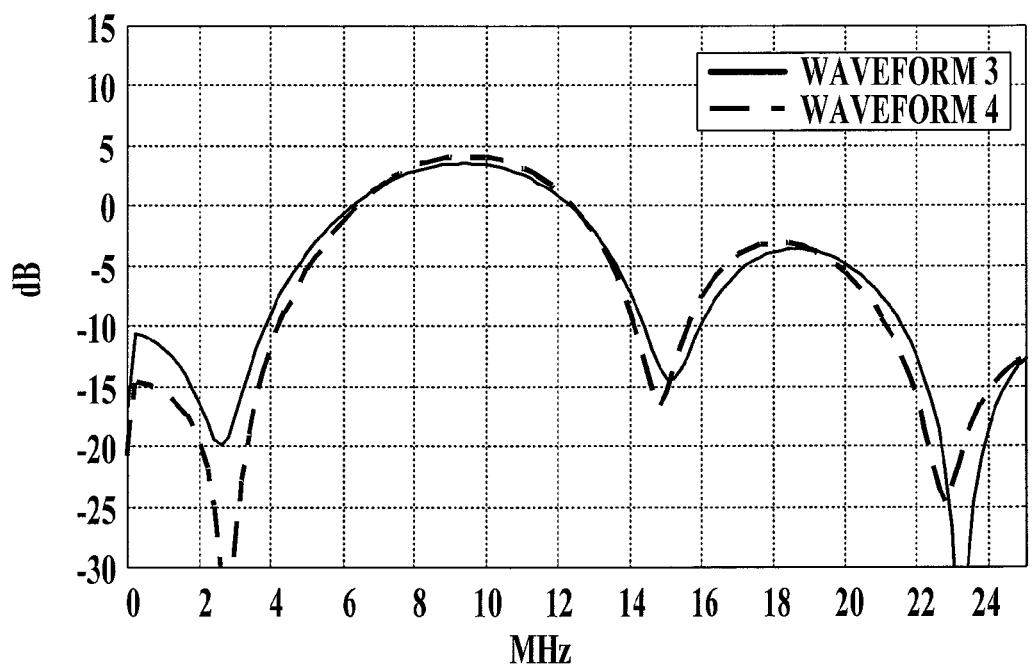
FIG. 24B is a drawing for explaining results of performing frequency analysis on the drive waveforms shown in FIG. 24A.

Further, the second pulse signal is a drive signal of waveform No. 4 as shown in FIG. 9. The drive signal of waveform No. 4 shows that the voltage starts decreasing at 0 nsec, reaches −HV at 7 nsec and maintains −HV until 32 nsec (the first duty). Thereafter, the voltage starts increasing at 32 nsec, reaches −HV at 38 nsec, maintains +HV until 75 nsec (the second duty). Thereafter, the voltage starts decreasing at 75 nsec, reaches 0V at 82 nsec and maintains 0V until 100 nsec (the third duty). Thereafter, the voltage starts decreasing at 100 nsec, reaches −HV at 107 nsec and maintains −HV until 138 nsec (the fourth duty). Thereafter, the voltage starts increasing at 138 nsec, reaches +MV at 144 nsec and maintains +MV until 169 nsec (the fifth duty). Thereafter, the voltage starts decreasing at 169 nsec and reaches 0V at 174 nsec. In such way, the drive duration of the drive signal of waveform No. 4 is 174 nsec, the drive duration being longer by 11 nsec comparing to the drive signal of waveform No. 3. Further, as shown in FIG. 24A, the waveform of the drive signal of waveform No. 4 which is the second pulse signal is time symmetric to the waveform of the drive signal of waveform No. 3. However, comparing to the length of the first duty in the waveform No. 3, the length of the fifth duty in the waveform No. 4 corresponding to the first duty in the waveform No. 3 is longer by 13 nsec. The frequency power spectrums obtained by performing frequency analysis on these drive waveforms are shown in FIG. 24B. In FIG. 24A, the horizontal axis indicates time and the vertical axis indicates voltage. In FIG. 24B, the horizontal axis indicates frequency and the vertical axis indicates signal intensity. The correlation coefficient of these frequency power spectrums in the transmission frequency band (3.8 MHz-18.6 MHz) at −20 dB of the ultrasound probe A is 0.973.

Embodiment Examples 3

First, as the above described ultrasound probe 2, an ultrasound probe having the following characteristics is used, the characteristics being: the minimum frequency (FL20) at −20 dB in transmission is 5.0 MHz, the maximum frequency (FH20) at −20 dB in transmission is 17.8 MHz, the center frequency (FC20) is 11.2 MHz and the fractional bandwidth at −20 dB in transmission is 114%. This ultrasound probe is referred to as the ultrasound probe B. The line B in FIG. 5 shows the transmission bandwidth shape of the ultrasound probe B.

The first pulse signal and the second pulse signal output from the transmission unit 12 are the same as the drive signal of waveform No. 3 and the drive signal of waveform No. 4, respectively, in Embodiment example 2. The correlation coefficient of the frequency power spectrums of these drive signals in the transmission frequency band (5.0 MHz-17.8 MHz) at −20 dB of the ultrasound probe B is 0.977.

Embodiment Example 4

First, as the above described ultrasound probe 2, an ultrasound probe having the following characteristics is used, the characteristics being: the minimum frequency (FL20) at −20 dB in transmission is 5.6 MHz, the maximum frequency (FH20) at −20 dB in transmission is 17.3 MHz, the center frequency (FC20) is 11.2 MHz and the fractional bandwidth at −20 dB in transmission is 104%. This ultrasound probe is referred to as the ultrasound probe C. The line C in FIG. 5 shows the transmission bandwidth shape of the ultrasound probe C.

The first pulse signal and the second pulse signal output from the transmission unit 12 are the same as the drive signal of waveform No. 3 and the drive signal of waveform No. 4, respectively, in Embodiment example 2. The correlation coefficient of the frequency power spectrums of these drive signals in the transmission frequency band (5.0 MHz-17.8 MHz) at −20 dB of the ultrasound probe B is 0.977.

Embodiment Example 5

First, as for the ultrasound probe 2, the ultrasound probe A same as that in Embodiment example 1 is used.

The first pulse signal output from the transmission unit 12 is a drive signal of waveform No. 3 same as that in Embodiment example 1.

Figure 10:
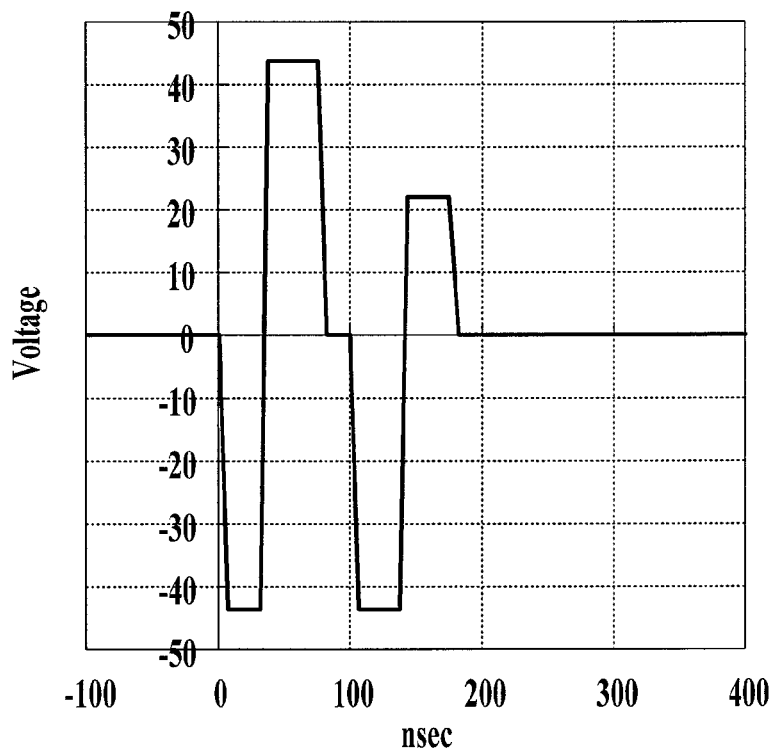
FIG. 10 is a drawing for explaining a drive waveform of a pulse signal, the drive waveform being referred to as waveform No. 5.
Figure 25A:
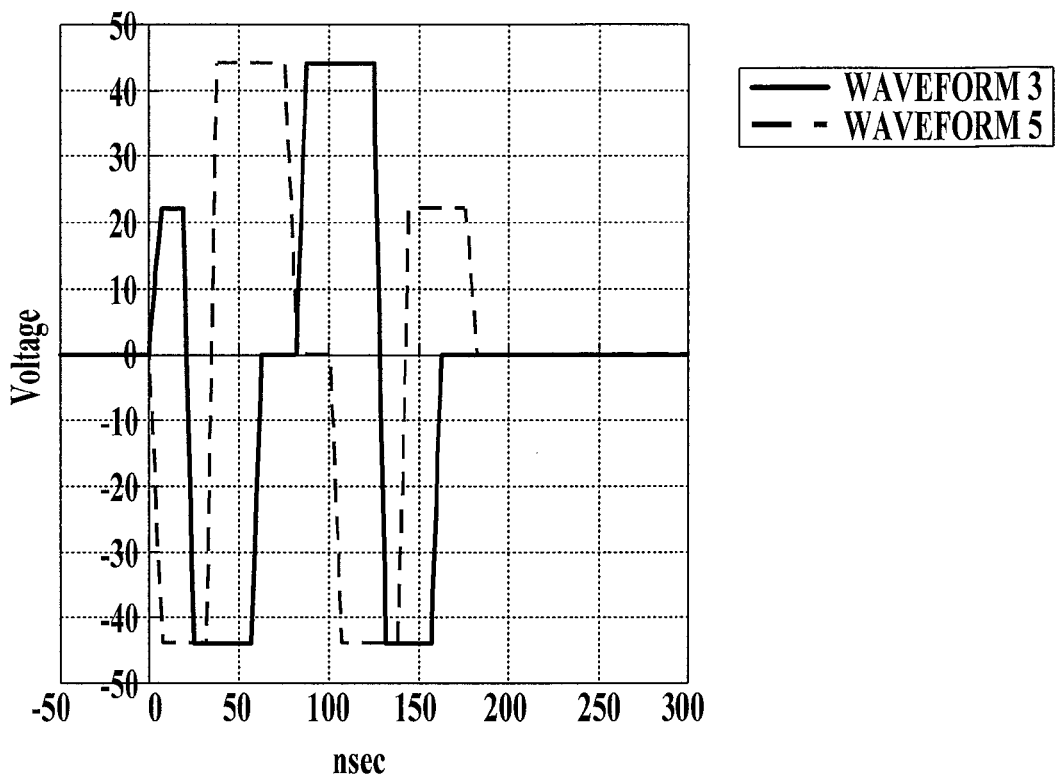
FIG. 25A is a drawing for explaining drive waveforms of pulse signals.
Figure 25B:
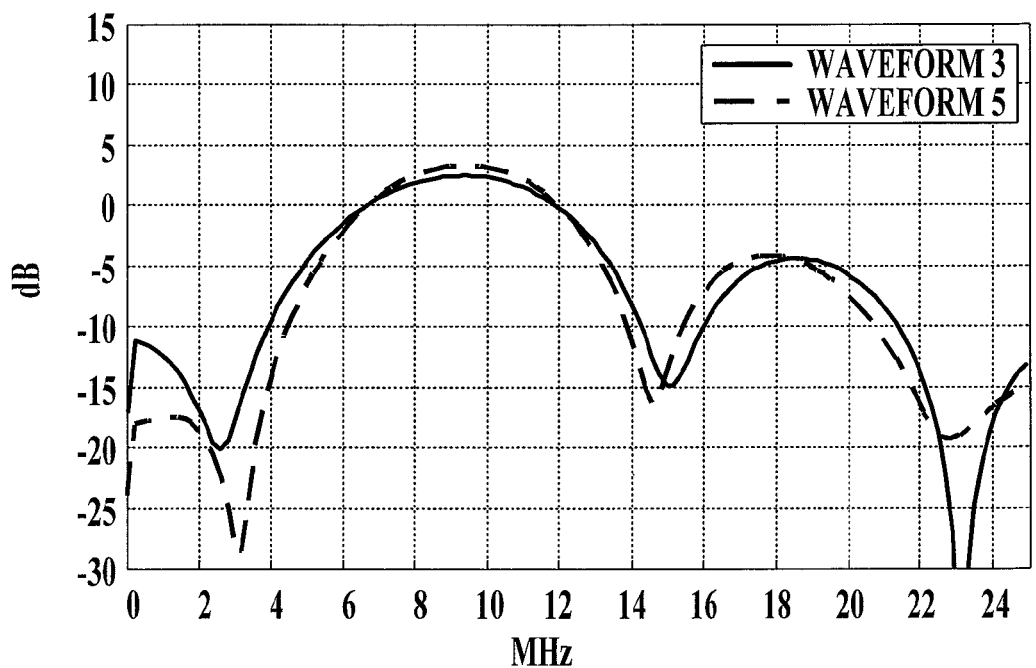
FIG. 25B is a drawing for explaining results of performing frequency analysis on the drive waveforms shown in FIG. 25A.

The second pulse signal is a drive signal of waveform No. 5 as shown in FIG. 10. The drive signal of waveform No. 5 shows that the voltage starts decreasing at 0 nsec, reaches −HV at 7 nsec and maintains −HV until 32 nsec (the first duty). Thereafter, the voltage starts increasing at 32 nsec, reaches +HV at 38 nsec and maintains +HV until 75 nsec (the second duty). Thereafter, the voltage starts decreasing at 75 nsec, reaches 0V at 82 nsec and maintains 0V until 100 nsec (the third duty). Thereafter, the voltage starts decreasing at 100 nsec, reaches −HV at 107 nsec and maintains −HV until 138 nsec (the fourth duty). Thereafter, the voltage starts increasing at 138 nsec, reaches +MV at 144 nsec and maintains +MV until 175 nsec (the fifth duty). Thereafter, the voltage starts decreasing at 175 nsec and reached 0V at 182 nsec. In such way, the drive duration of the drive signal of waveform No. 5 is 182 nsec, the drive duration being longer by 19 nsec comparing to the drive signal of waveform No. 3. Further, as shown in FIG. 25A, the waveform of the drive signal of waveform No. 5 which is the second pulse signal is time symmetric to the waveform of the drive signal of wave form No. 3. However, comparing to the length of the first duty in the waveform No. 3, the length of the fifth duty in the waveform No. 5 corresponding to the first duty in the waveform No. 3 is longer by 19 nsec. The frequency power spectrums obtained by performing frequency analysis on these drive waveforms are shown in FIG. 25B. In FIG. 25A, the horizontal axis indicates time and the vertical axis indicates voltage. In FIG. 25B, the horizontal axis indicates frequency and the vertical axis indicates signal intensity. The correlation coefficient of these frequency power spectrums in the transmission frequency band (3.8 MHz-18.6 MHz) at −20 dB of the ultrasound probe A is 0.942.

Embodiment Example 6

First, as for the ultrasound probe 2, the ultrasound probe A same as that in Embodiment example 1 is used.

The first pulse signal output from the transmission unit 12 is a drive signal of waveform No. 3 same as that in Embodiment example 1.

Figure 11:
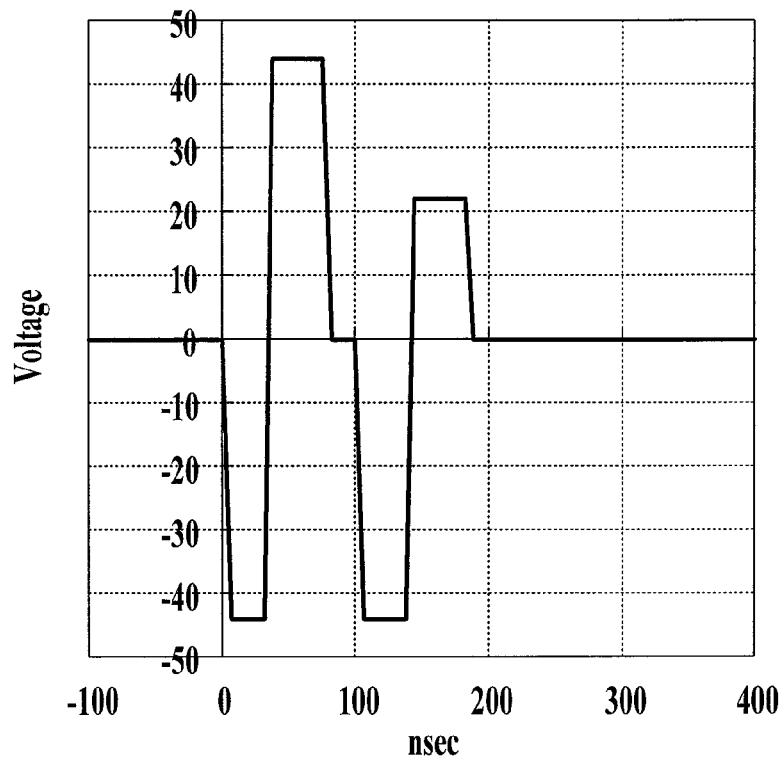
FIG. 11 is a drawing for explaining a drive waveform of a pulse signal, the drive waveform being referred to as waveform No. 6.
Figure 26A:
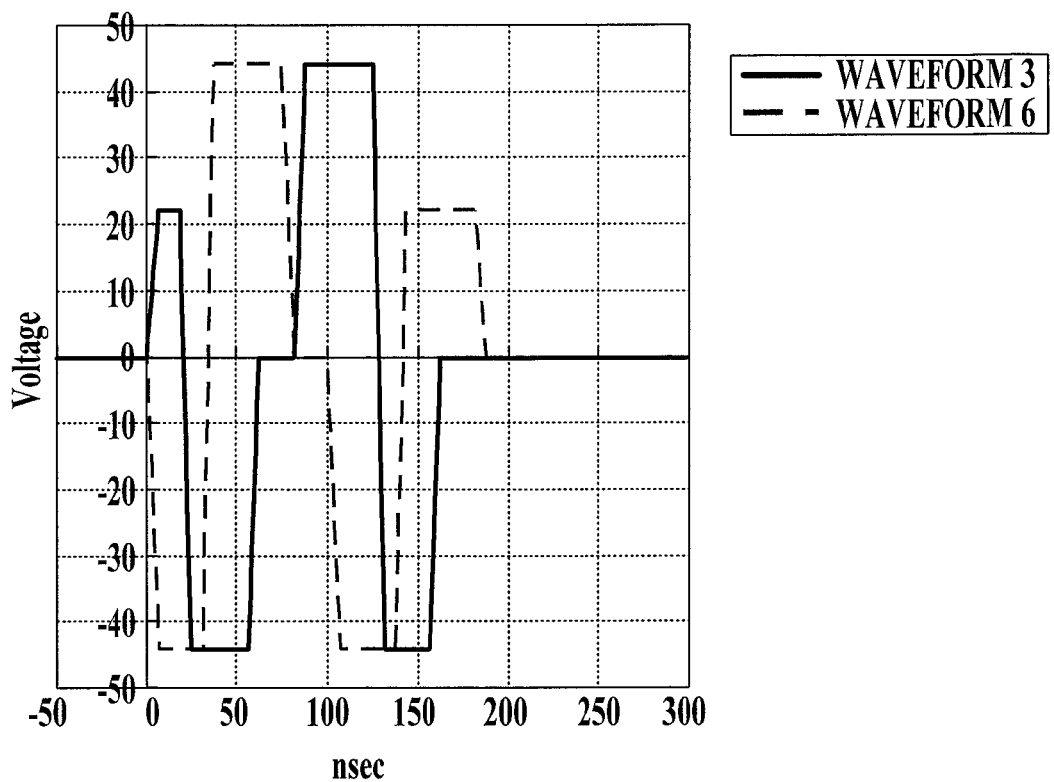
FIG. 26A is a drawing for explaining drive waveforms of pulse signals.
Figure 26B:
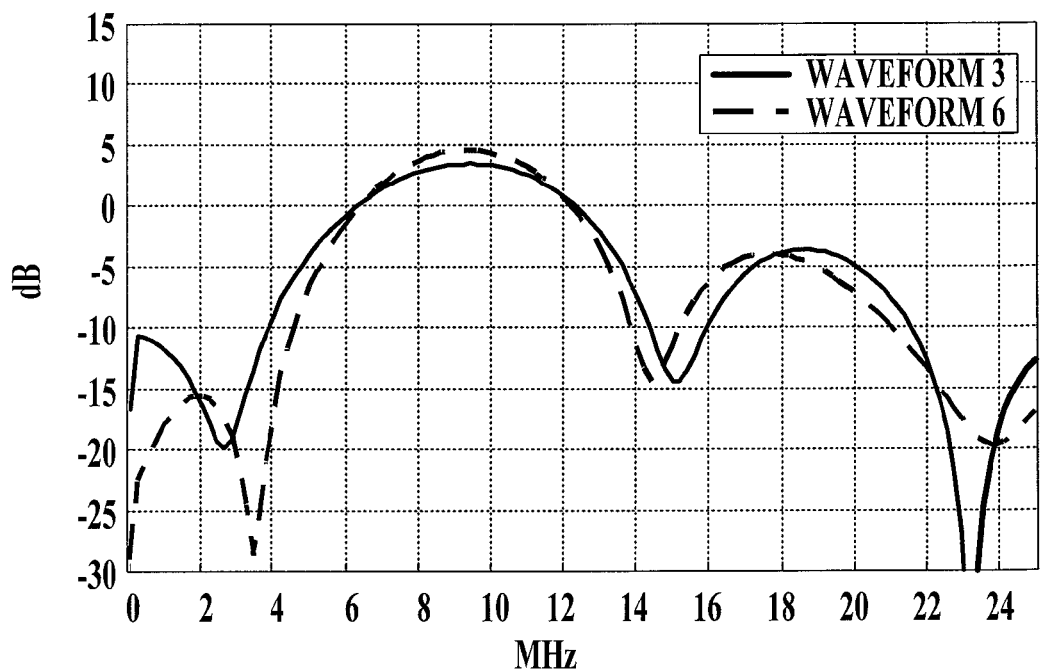
FIG. 26B is a drawing for explaining results of performing frequency analysis on the drive waveforms shown in FIG. 26A.

Further, the second pulse signal is a drive signal of waveform No. 6 as shown in FIG. 11. The drive signal of waveform No. 6 shows that the voltage starts decreasing at 0 nsec, reaches −HV at 7 nsec and maintains −HV until 32 nsec (the first duty). Thereafter, the voltage starts increasing at 32 nsec, reaches +HV at 38 nsec and maintains +HV until 75 nsec (the second duty). Thereafter, the voltage starts decreasing at 75 nsec, reaches 0V at 82 nsec and maintains 0V until 100 nsec (the third duty). Thereafter, the voltage starts decreasing at 100 nsec, reaches −HV at 107 nsec and maintains −HV until 138 nsec (the fourth duty). Thereafter, the voltage starts increasing at 138 nsec, reaches +MV at 144 nsec and maintains +MV until 182 nsec (the fifth duty). Thereafter, the voltage starts decreasing at 182 nsec and reaches 0V at 188 nsec. In such way, the drive duration of the drive signal of waveform No. 6 is 188 nsec, the drive duration being longer by 25 nsec comparing to the drive signal of waveform No. 3. Further, as shown in FIG. 26A, the waveform of the drive signal of waveform No. 6 which is the second pulse signal is time symmetric to the waveform of the drive signal of waveform No. 3. However, comparing to the length of the first duty in the waveform No. 3, the length of the fifth duty in the waveform No. 6 corresponding to the first duty in the waveform No. 3 is longer by 26 nsec. The frequency power spectrums obtained by performing frequency analysis on these drive waveforms are shown in FIG. 26B. In FIG. 26A, the horizontal axis indicates time and the vertical axis indicates voltage. In FIG. 26B, the horizontal axis indicates frequency and the vertical axis indicates signal intensity. The correlation coefficient of these frequency power spectrums in the transmission frequency band (3.8 MHz-18.6 MHz) at −20 dB of the ultrasound probe A is 0.905.

Embodiment Example 7

First, as for the ultrasound probe 2, the ultrasound probe A same as that in Embodiment example 1 is used.

The first pulse signal output from the transmission unit 12 is a drive signal of waveform No. 3 same as that in Embodiment example 1.

Figure 12:
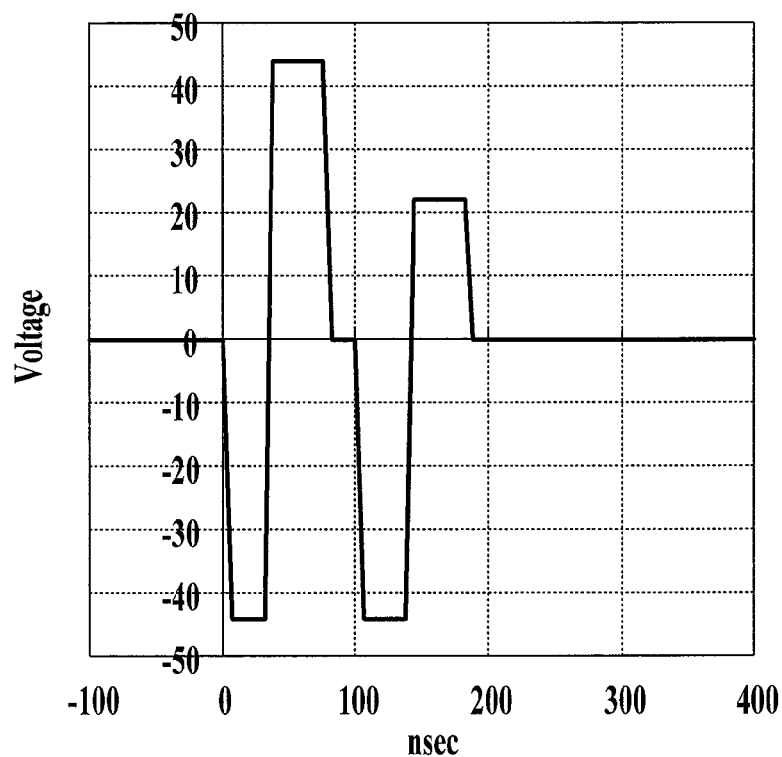
FIG. 12 is a drawing for explaining a drive waveform of a pulse signal, the drive waveform being referred to as waveform No. 7.
Figure 27A:
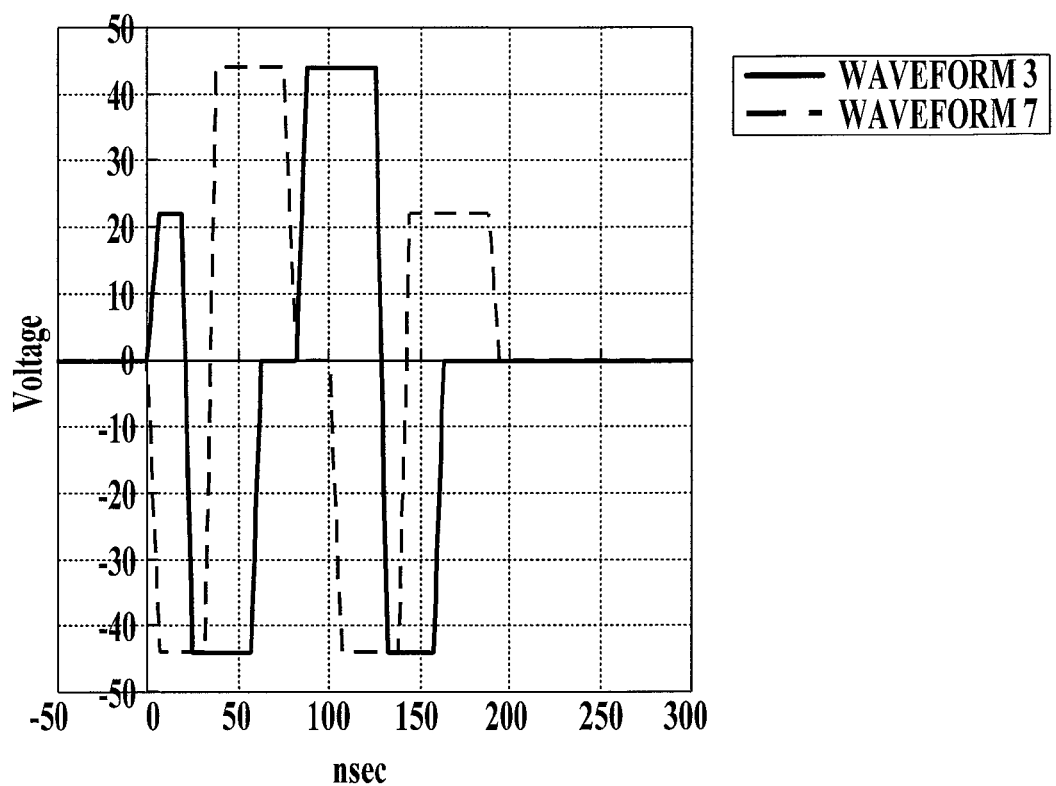
FIG. 27A is a drawing for explaining drive waveforms of pulse signals.
Figure 27B:
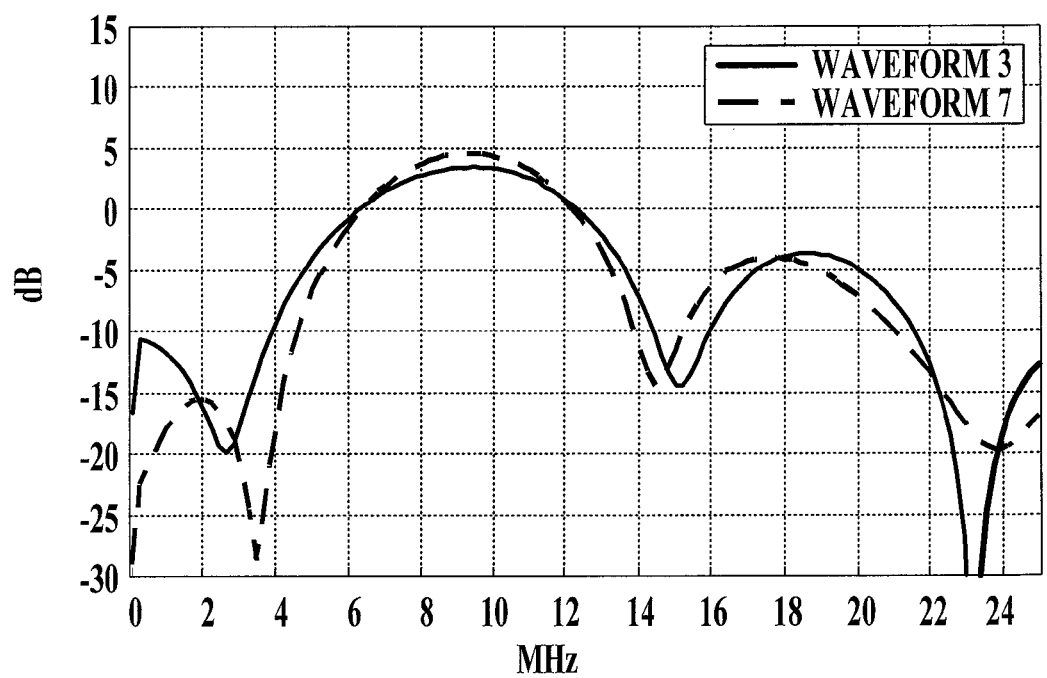
FIG. 27B is a drawing for explaining results of performing frequency analysis on the drive waveforms shown in FIG. 27A.

Further, the second pulse signal is a drive signal of waveform No. 7 as shown in FIG. 12. The drive signal of waveform No. 7 shows that the voltage starts decreasing at 0 nsec, reaches −HV at 7 nsec and maintains −HV until 32 nsec (the first duty). Thereafter, the voltage starts increasing at 32 nsec, reaches +HV at 38 nsec and maintains +HV until 75 nsec (the second duty). Thereafter, the voltage starts decreasing at 75 nsec, reaches 0V at 82 nsec and maintains 0V until 100 nsec (the third duty). Thereafter, the voltage starts decreasing at 100 nsec, reaches −HV at 107 nsec and maintains −HV until 138 nsec (the fourth duty). Thereafter, the voltage starts increasing at 138 nsec, reaches +MV at 144 nsec and maintains +MV until 188 nsec (the fifth duty). Thereafter, the voltage starts decreasing at 188 nsec and reaches 0V at 194 nsec. In such way, the drive duration of the drive signal of waveform No. 7 is 194 nsec, the drive duration being longer by 31 nsec comparing to the drive signal of waveform No. 3. Further, as shown in FIG. 27A, the waveform of the drive signal of waveform No. 7 which is the second pulse signal is time symmetric to the waveform of the drive signal of wave form No. 3. However, comparing to the length of the first duty in the waveform No. 3, the length of the fifth duty in the waveform No. 7 corresponding to the first duty in the waveform No. 3 is longer by 32 nsec. The frequency power spectrums obtained by performing frequency analysis on these drive waveforms are shown in FIG. 27B. In FIG. 27A, the horizontal axis indicates time and the vertical axis indicates voltage. In FIG. 27B, the horizontal axis indicates frequency and the vertical axis indicates signal intensity. The correlation coefficient of these frequency power spectrums in the transmission frequency band (3.8 MHz-18.6 MHz) at −20 dB of the ultrasound probe A is 0.859.

Embodiment Example 8

First, as for the ultrasound probe 2, the ultrasound probe A same as that in Embodiment example 1 is used.

The first pulse signal output from the transmission unit 12 is a drive signal of waveform No. 3 same as that in Embodiment example 1.

Figure 13:
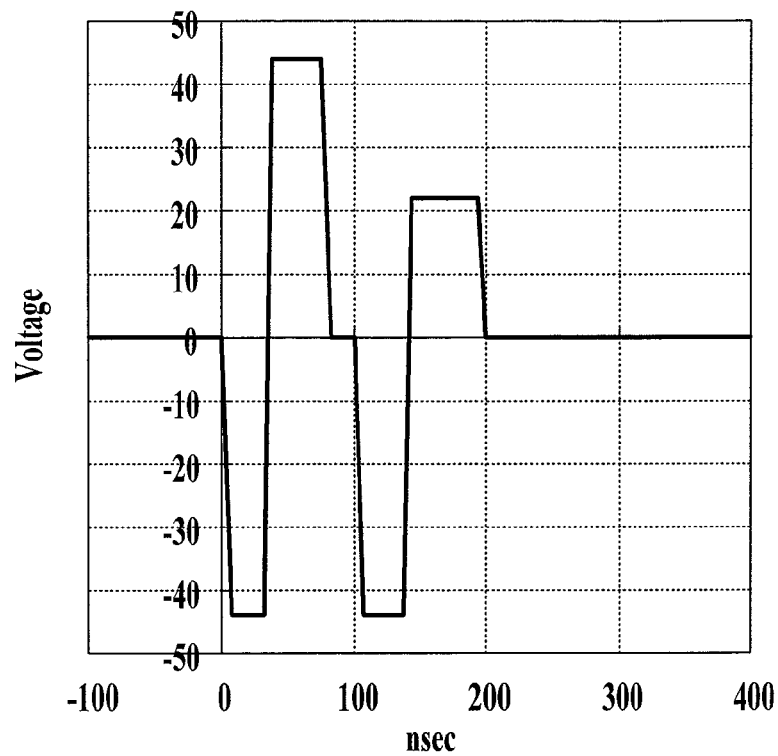
FIG. 13 is a drawing for explaining a drive waveform of a pulse signal, the drive waveform being referred to as waveform No. 8.
Figure 28A:
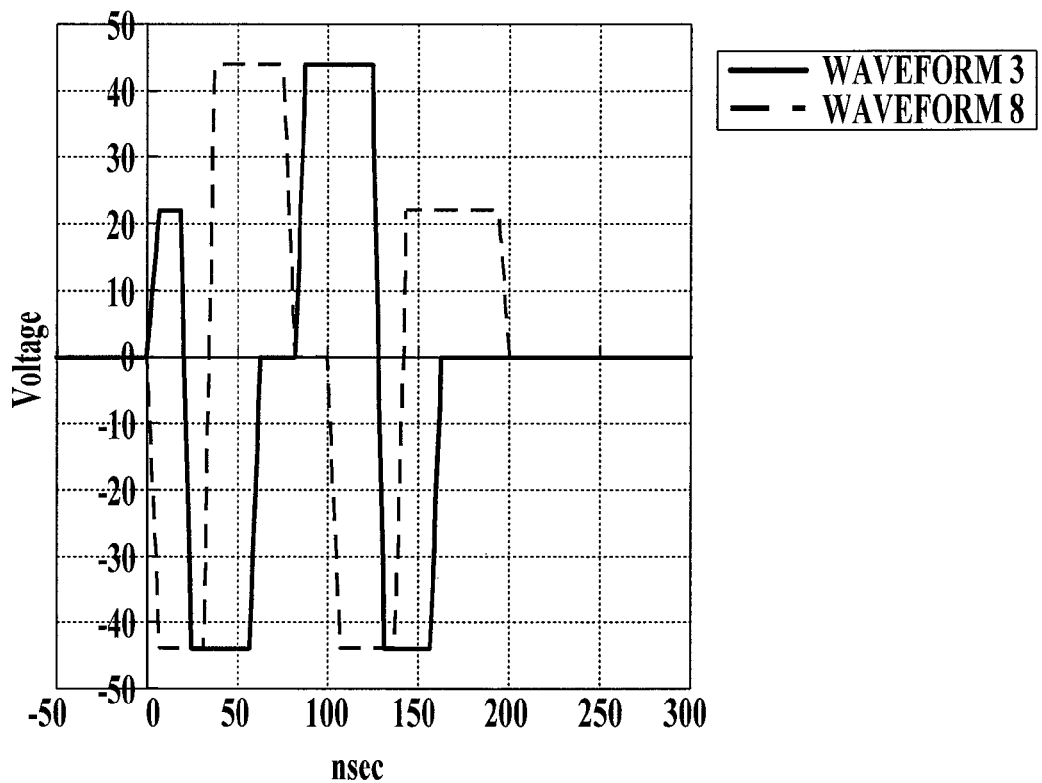
FIG. 28A is a drawing for explaining drive waveforms of pulse signals.
Figure 28B:
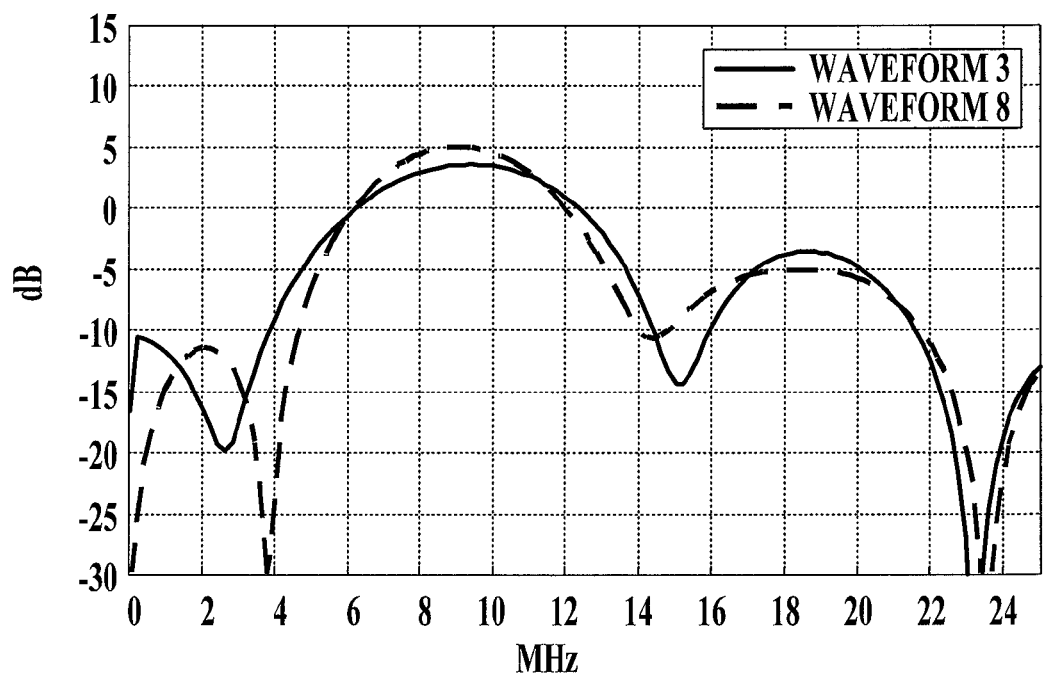
FIG. 28B is a drawing for explaining results of performing frequency analysis on the drive waveforms shown in FIG. 28A.

Further, the second pulse signal is a drive signal of waveform No. 8 as shown in FIG. 13. The drive signal of waveform No. 8 shows that the voltage starts decreasing at 0 nsec, reaches −HV at 7 nsec and maintains −HV until 32 nsec (the first duty). Thereafter, the voltage starts increasing at 32 nsec, reaches +HV at 38 nsec and maintains +HV until 75 nsec (the second duty). Thereafter, the voltage starts decreasing at 75 nsec, reaches 0V at 82 nsec and maintains 0V until 100 nsec (the third duty). Thereafter, the voltage starts decreasing at 100 nsec, reaches −HV at 107 nsec and maintains −HV until 138 nsec (the fourth duty). Thereafter, the voltage starts increasing at 138 nsec, reaches +MV at 144 nsec and maintains +MV until 194 nsec (the fifth duty). Thereafter, the voltage starts decreasing at 194 nsec and reaches 0V at 200 nsec. In such way, the drive duration of the drive signal of waveform No. 8 is 200 nsec, the drive duration being longer by 37 nsec comparing to the drive signal of waveform No. 3. Further, as shown in FIG. 28A, the waveform of the drive signal of waveform No. 8 which is the second pulse signal is time symmetric to the waveform of the drive signal of waveform No. 3. However, comparing to the length of the first duty in the waveform No. 3, the length of the fifth duty in the waveform No. 8 corresponding to the first duty in the waveform No. 3 is longer by 38 nsec. The frequency power spectrums obtained by performing frequency analysis on these drive waveforms are shown in FIG. 28B. In FIG. 28A, the horizontal axis indicates time and the vertical axis indicates voltage. In FIG. 28B, the horizontal axis indicates frequency and the vertical axis indicates signal intensity. The correlation coefficient of these frequency power spectrums in the transmission frequency band (3.8 MHz-18.6 MHz) at −20 dB of the ultrasound probe A is 0.835.

Embodiment Example 9

First, as for the ultrasound probe 2, the ultrasound probe A same as that in Embodiment example 1 is used.

Figure 15:
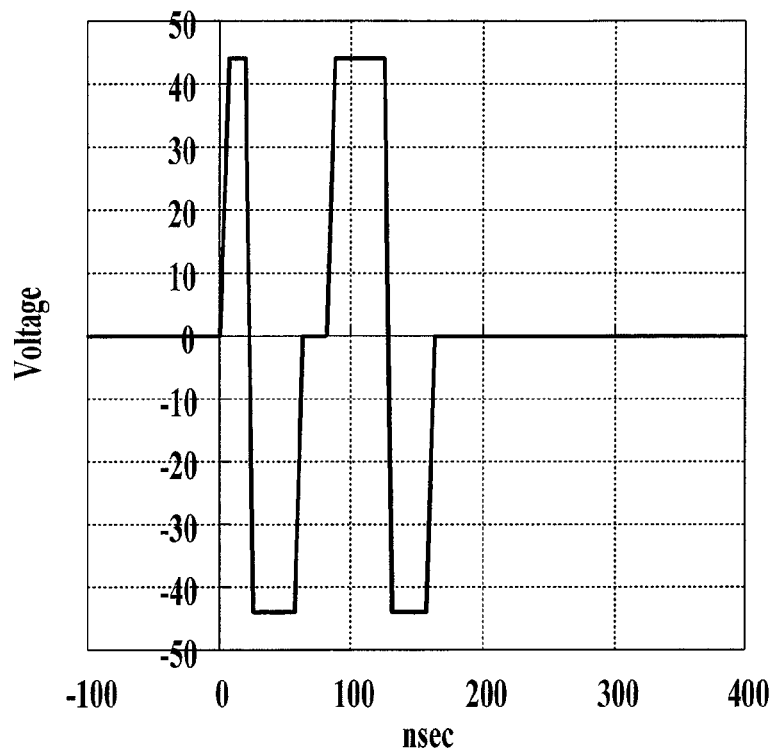
FIG. 15 is a drawing for explaining a drive waveform of a pulse signal, the drive waveform being referred to as waveform No. 10.

The first pulse signal output from the transmission unit 12 is a drive signal of waveform No. 10 as shown in FIG. 15. The drive signal of waveform No. 10 shows that the voltage starts increasing at 0 nsec, reaches +HV at 7 nsec and maintains +HV until 19 nsec (the first duty). Thereafter, the voltage starts decreasing at 19 nsec, reaches −HV at 25 nsec and maintains −HV until 57 nsec (the second duty). Thereafter, the voltage starts increasing at 57 nsec, reaches 0V at 63 nsec and maintains 0V until 82 nsec (the third duty). Thereafter, the voltage starts increasing at 82 nsec, reaches +HV at 88 nsec and maintains +HV at 125 nsec (the fourth duty). Thereafter, the voltage starts decreasing at 125 nsec, reaches −HV at 132 nsec and maintains −HV until 157 nsec (the fifth duty). Thereafter, the voltage starts increasing at 157 nsec and reaches 0V at 163 nsec. In such way, the drive duration of the drive signal of waveform No. 10 is 163 nsec.

Figure 22:
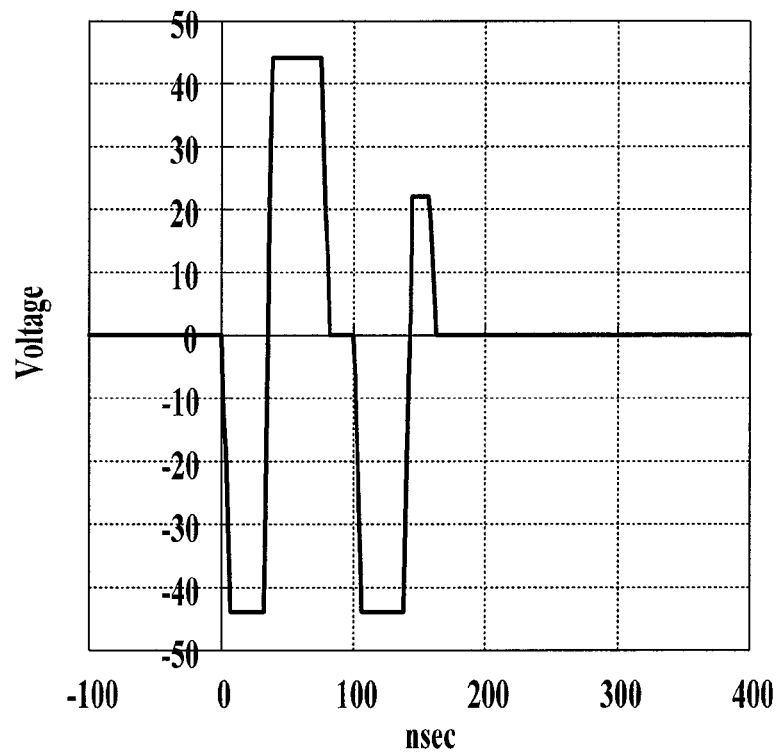
FIG. 22 is a drawing for explaining a drive waveform of a pulse signal, the drive waveform being referred to as waveform No. 17.
Figure 29A:
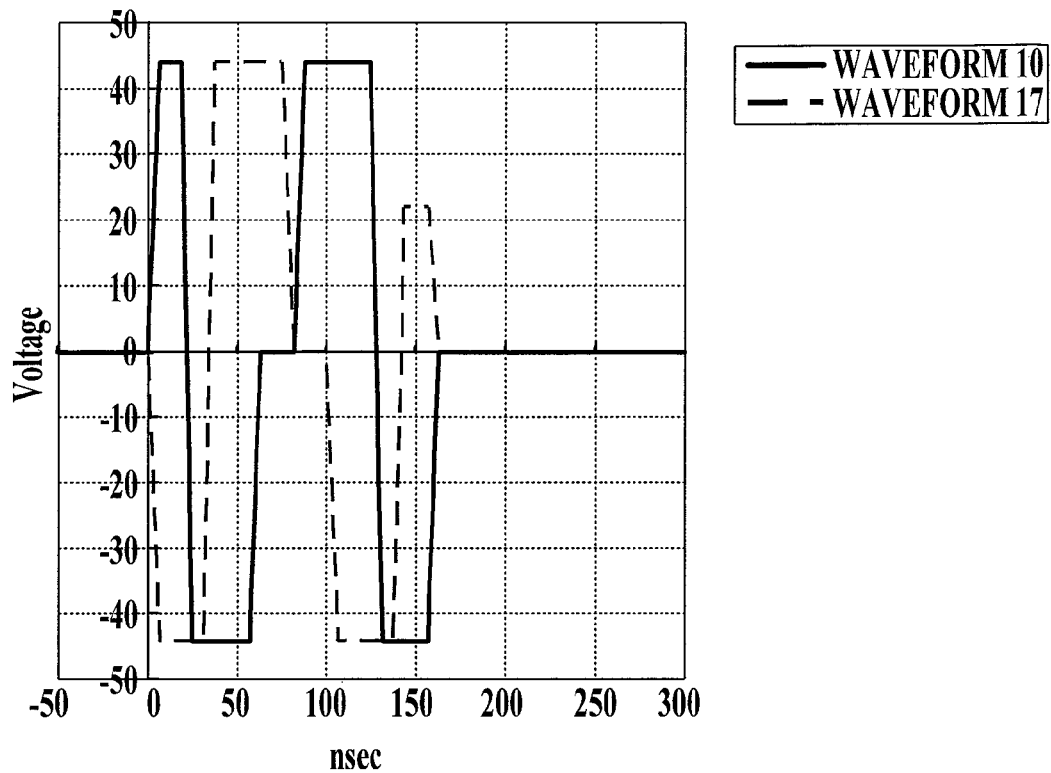
FIG. 29A is a drawing for explaining drive waveforms of pulse signals.
Figure 29B:
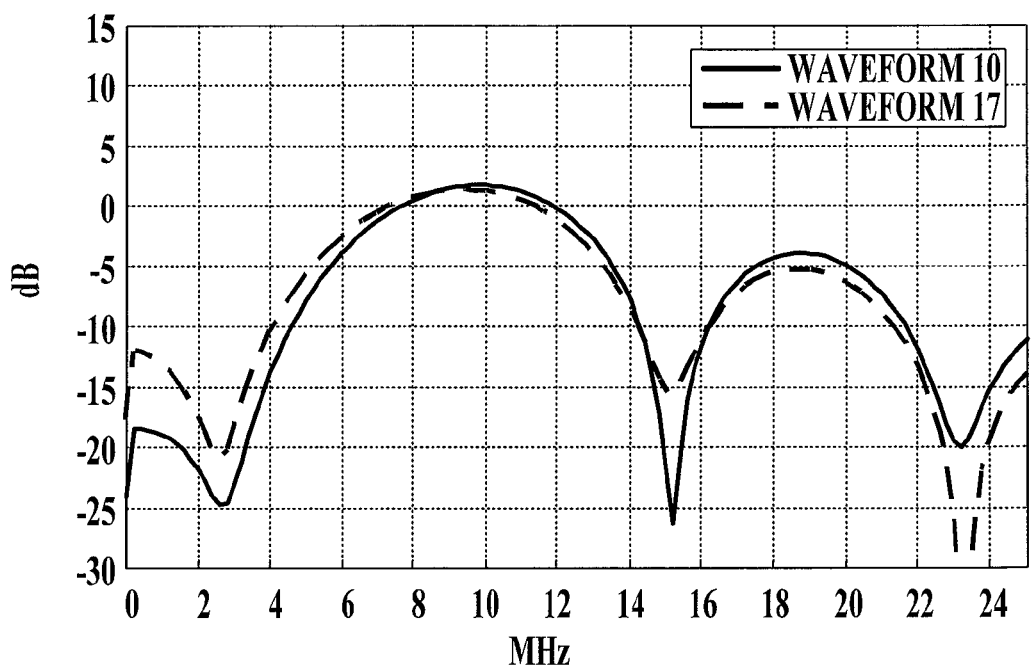
FIG. 29B is a drawing for explaining results of performing frequency analysis on the drive waveforms shown in FIG. 29A.

Further, the second pulse signal is a drive signal of waveform No. 17 as shown in FIG. 22. The drive signal of waveform No. 17 shows that the voltage starts decreasing at 0 nsec, reaches −HV at 7 nsec and maintains −HV until 32 nsec (the first duty). Thereafter, the voltage starts increasing at 32 nsec, reaches +HV at 38 nsec and maintains +HV until 75 nsec (the second duty). Thereafter, the voltage starts decreasing at 75 nsec, reaches 0V at 82 nsec and maintains 0V until 100 nsec (the third duty). Thereafter, the voltage starts decreasing at 100 nsec, reaches −HV at 107 nsec and maintains −HV until 138 nsec (the fourth duty). Thereafter, the voltage starts increasing at 138 nsec, reaches +MV at 144 nsec and maintains +MV until 157 nsec (the fifth duty). Thereafter, the voltage starts decreasing at 157 nsec and reaches 0V at 163 nsec. In such way, the drive duration of the drive signal of waveform No. 17 is 163 nsec, the drive duration being the same as that of the drive signal of waveform No. 10. Further, as shown in FIG. 29A, the waveform of the drive signal of waveform No. 17 which is the second pulse signal is time symmetric to the waveform of the drive signal of wave form No. 10. However, the voltage at the first duty in the waveform No. 10 is higher than the voltage at the fifth duty in the waveform No. 17 corresponding to the first duty in the waveform No. 10. The frequency power spectrums obtained by performing frequency analysis on these drive waveforms are shown in FIG. 29B. In FIG. 29A, the horizontal axis indicates time and the vertical axis indicates voltage. In FIG. 29B, the horizontal axis indicates frequency and the vertical axis indicates signal intensity. The correlation coefficient of these frequency power spectrums in the transmission frequency band (3.8 MHz-18.6 MHz) at −20 dB of the ultrasound probe A is 0.961.

Embodiment Example 10

First, as for the ultrasound probe 2, the ultrasound probe A same as that in Embodiment example 1 is used.

Figure 18:
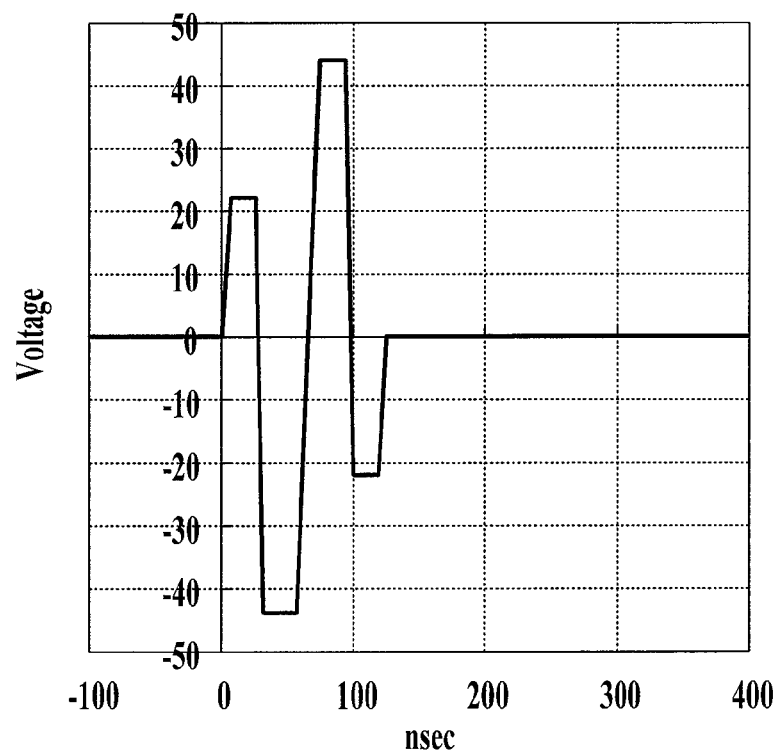
FIG. 18 is a drawing for explaining a drive waveform of a pulse signal, the drive waveform being referred to as waveform No. 13.

The first pulse signal output from the transmission unit 12 is a drive signal of waveform No. 13 as shown in FIG. 18. The drive signal of waveform No. 13 shows that the voltage starts increasing at 0 nsec, reaches +MV at 7 nsec and maintains +MV until 25 nsec (the first duty). Thereafter, the voltage starts decreasing at 25 nsec, reaches −HV at 32 nsec and maintains −HV until 57 nsec (the second duty). Thereafter, the voltage starts increasing at 57 nsec, reaches +HV at 75 nsec and maintains +HV until 94 nsec (the third duty). Thereafter, the voltage starts decreasing at 94 nsec, reaches −MV at 100 nsec and maintains −MV until 119 nsec (the fourth duty). Thereafter, the voltage starts increasing at 119 nsec and reaches 0V at 125 nsec. In such way, the drive duration of the drive signal of waveform No. 13 is 125 nsec.

Figure 19:
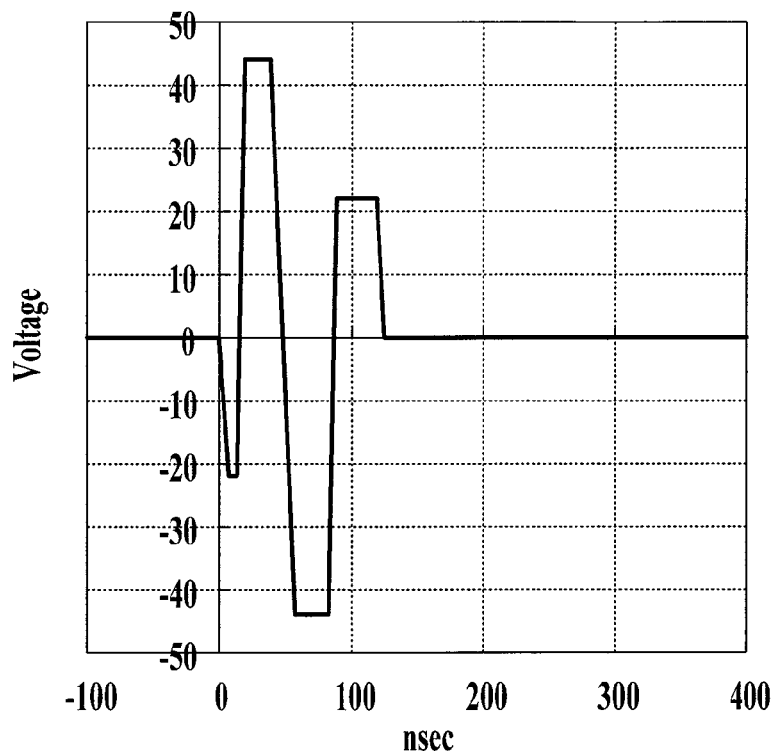
FIG. 19 is a drawing for explaining a drive waveform of a pulse signal, the drive waveform being referred to as waveform No. 14.
Figure 30A:
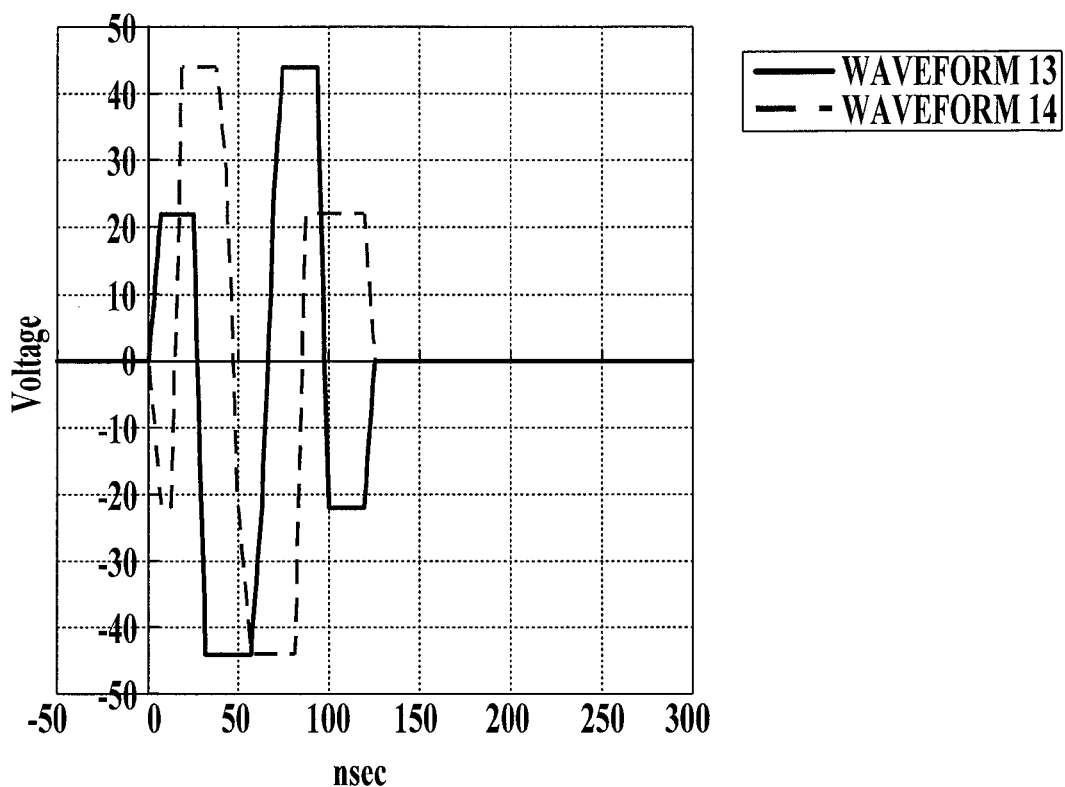
FIG. 30A is a drawing for explaining drive waveforms of pulse signals.
Figure 30B:
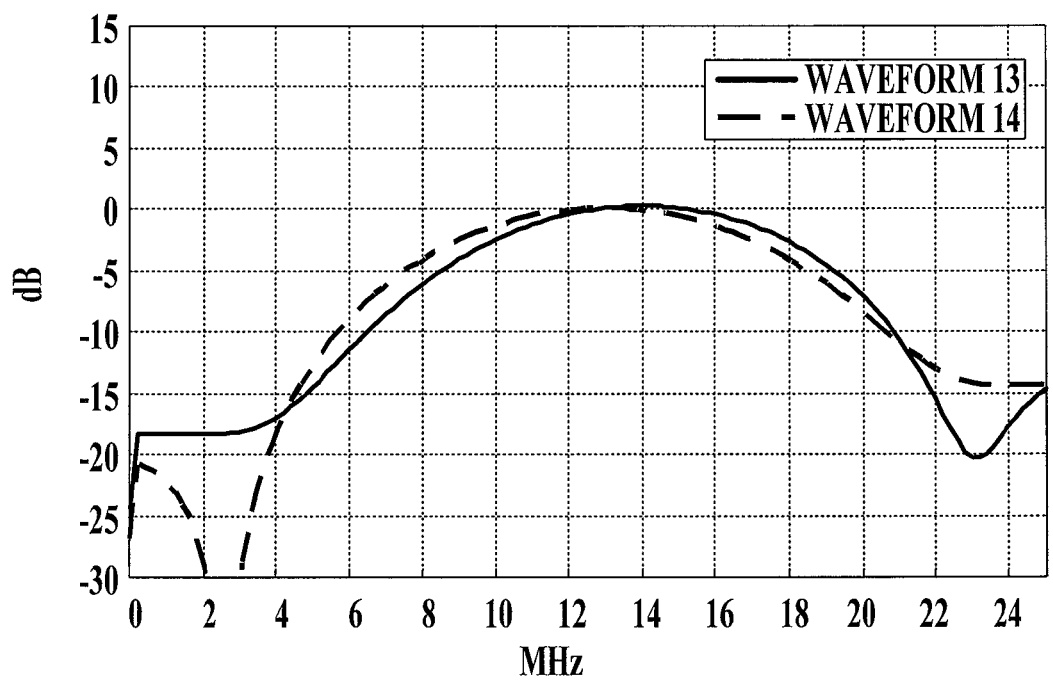
FIG. 30B is a drawing for explaining results of performing frequency analysis on the drive waveforms shown in FIG. 30A.

Further, the second pulse signal is a drive signal of waveform No. 14 as shown in FIG. 19. The drive signal of waveform No. 14 shows that the voltage starts decreasing at 0 nsec, reaches −MV at 7 nsec and maintains −MV until 13 nsec (the first duty). Thereafter, the voltage starts increasing at 13 nsec, reaches +HV at 19 sec and maintains +HV until 38 nsec (the second duty). Thereafter, the voltage starts decreasing at 38 nsec, reaches −HV at 57 nsec and maintains −HV until 82 nsec (the third duty). Thereafter, the voltage starts increasing at 82 nsec, reaches +MV at 88 nsec and maintains +MV until 119 nsec (the fourth duty). Thereafter, the voltage starts decreasing at 119 nsec and reaches 0V at 125 nsec. In such way, the drive duration of the drive signal of waveform No. 14 is 125 nsec, the drive duration being the same as that of the drive signal of waveform No. 13. Further, as shown in FIG. 30A, the waveform of the drive signal of waveform No. 14 which is the second pulse signal is time symmetric to the waveform of the drive signal of wave form No. 13. However, comparing to the length of the first duty in the waveform No. 13, the length of the fourth duty in the waveform No. 14 corresponding to the first duty in the waveform No. 13 is longer by 13 nsec. Further, comparing to the length of the fourth duty in the waveform No. 13, the length of the first duty in the waveform No. 14 corresponding to the fourth duty in the waveform No. 13 is shorter by 13 nsec. The frequency power spectrums obtained by performing frequency analysis on these drive waveforms are shown in FIG. 30B. In FIG. 30A, the horizontal axis indicates time and the vertical axis indicates voltage. In FIG. 30B, the horizontal axis indicates frequency and the vertical axis indicates signal intensity. The correlation coefficient of these frequency power spectrums in the transmission frequency band (3.8 MHz-18.6 MHz) at −20 dB of the ultrasound probe A is 0.965.

Embodiment Example 11

First, as for the ultrasound probe 2, the ultrasound probe A same as that in Embodiment example 1 is used.

Figure 16:
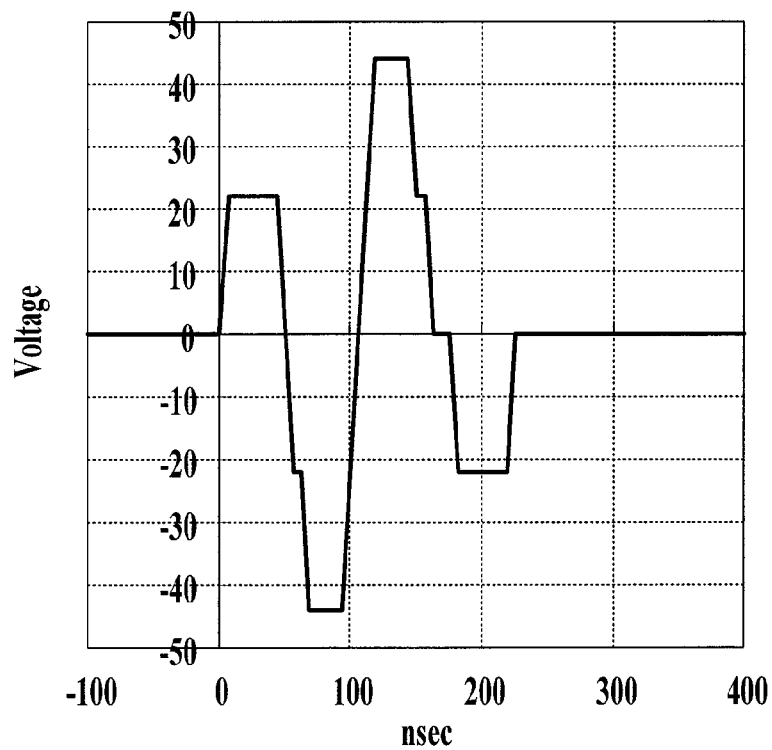
FIG. 16 is a drawing for explaining a drive waveform of a pulse signal, the drive waveform being referred to as waveform No. 11.

The first pulse signal output from the transmission unit 12 is a drive signal of waveform No. 11 as shown in FIG. 16. The drive signal of waveform No. 11 shows that the voltage starts increasing at 0 nsec, reaches +MV at 7 nsec and maintains +MV until 44 nsec (the first duty). Thereafter, the voltage starts decreasing at 44 nsec, reaches −MV at 57 nsec and maintains −MV until 63 nsec (the second duty). Thereafter, the voltage starts decreasing at 63 nsec, reaches −HV at 69 nsec and maintains −HV until 94 nsec (the third duty). Thereafter, the voltage starts increasing at 94 nsec, reaches +HV at 119 nsec and maintains +HV until 144 nsec (the fourth duty). Thereafter, the voltage starts decreasing at 144 nsec, reaches +MV at 150 nsec and maintains +MV until 157 nsec (the fifth duty). Thereafter, the voltage starts decreasing at 157 nsec, reaches 0V at 163 nsec and maintains 0V until 175 nsec (the sixth duty). Thereafter, the voltage starts decreasing at 175 nsec, reaches −MV at 182 nsec and maintains −MV until 219 nsec (the seventh duty). Thereafter, the voltage starts increasing at 219 nsec and reaches 0V at 225 nsec. In such way, the drive duration of the drive signal of waveform No. 11 is 225 nsec.

Figure 17:
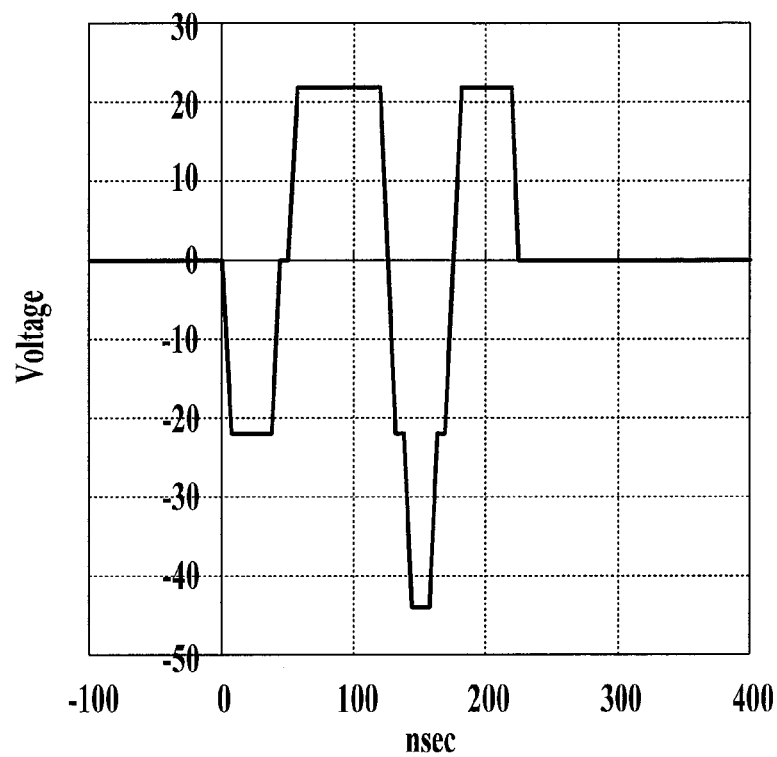
FIG. 17 is a drawing for explaining a drive waveform of a pulse signal, the drive waveform being referred to as waveform No. 12.
Figure 31A:
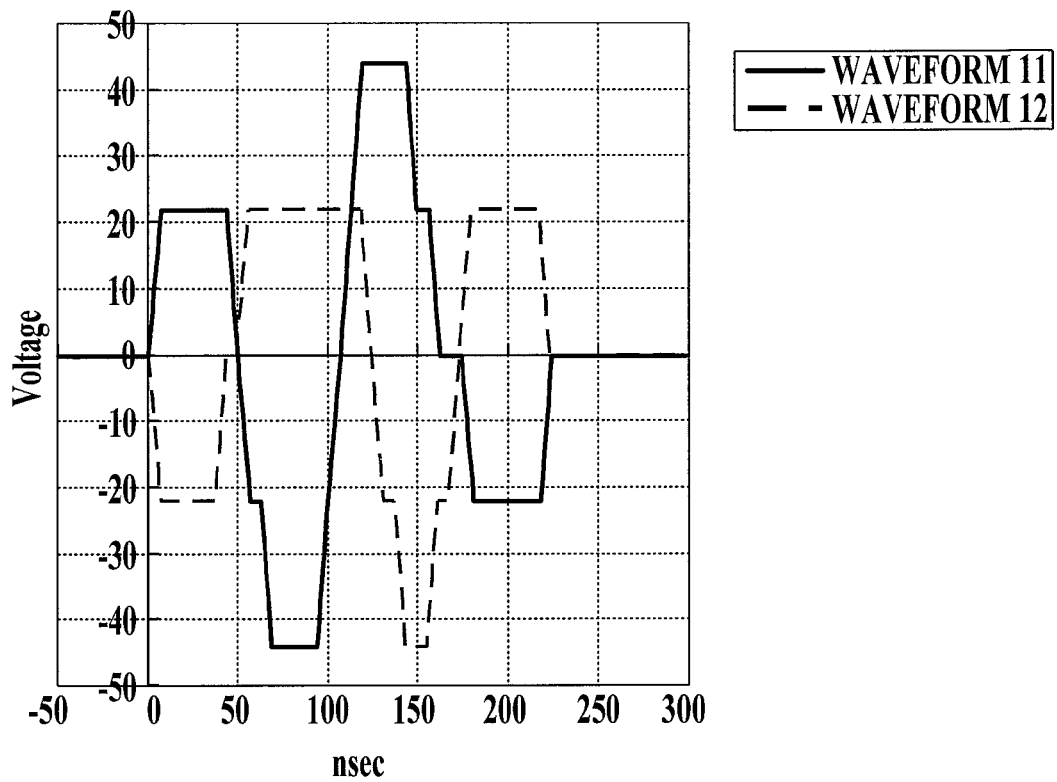
FIG. 31A is a drawing for explaining drive waveforms of pulse signals.
Figure 31B:
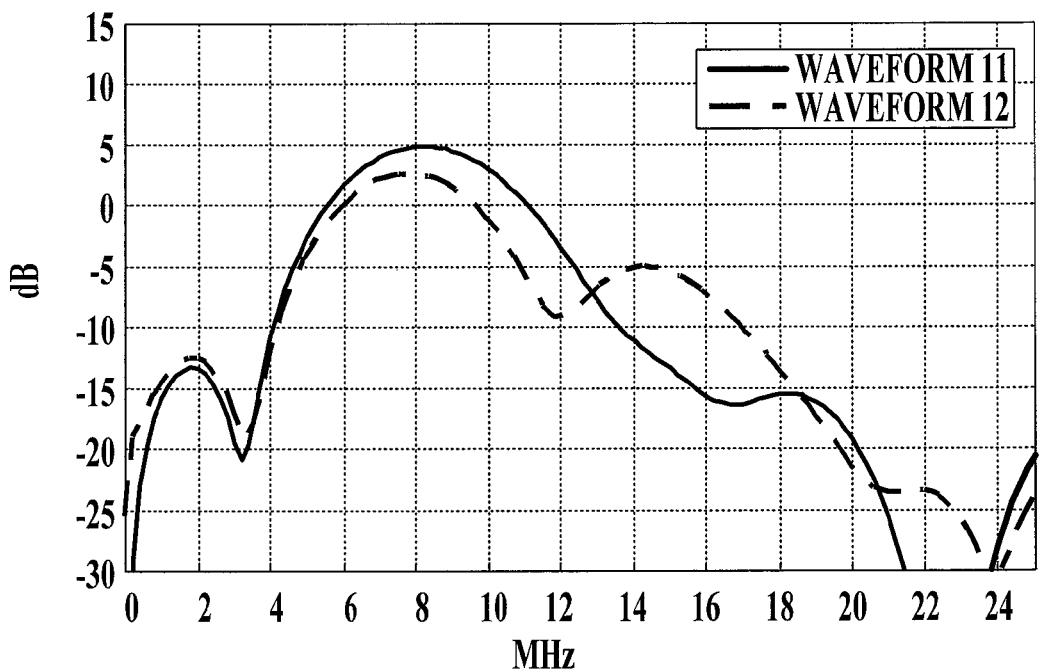
FIG. 31B is a drawing for explaining results of performing frequency analysis on the drive waveforms shown in FIG. 31A.

Further, the second pulse signal is a drive signal of waveform No. 12 as shown in FIG. 17. The drive signal of waveform No. 12 shows that the voltage starts decreasing at 0 nsec, reaches −MV at 7 nsec and maintains −MV until 38 nsec (the first duty). Thereafter, the voltage starts increasing at 38 nsec, reaches 0V at 44 nsec and maintains 0V until 50 nsec (the second duty). Thereafter, the voltage starts increasing at 50 nsec, reaches +MV at 57 nsec and maintains +MV until 119 nsec (the third duty). Thereafter, the voltage starts decreasing at 119 nsec, reaches −MV at 132 nsec and maintains −MV until 138 nsec (the fourth duty). Thereafter, the voltage starts decreasing at 138 nsec, reaches −HV at 144 nsec and maintains −HV until 157 nsec (the fifth duty). Thereafter, the voltage starts increasing at 157 nsec, reaches −MV at 163 nsec and maintains −MV until 169 nsec (the sixth duty). Thereafter, the voltage starts increasing at 169 nsec, reaches +MV at 182 nsec and maintains +MV until 219 nsec (the seventh duty). Thereafter, the voltage starts decreasing at 219 nsec and reaches 0V at 225 nsec. In such way, the drive duration of the drive signal of waveform No. 12 is 225 nsec, the drive duration being the same at that of the drive signal of waveform No. 11. Further, as shown in FIG. 31A, the waveform of the drive signal of waveform No. 12 which is the second pulse signal is asymmetric to the waveform of the drive signal of waveform No. 11. The frequency power spectrums obtained by performing frequency analysis on these drive waveforms are shown in FIG. 31B. In FIG. 31A, the horizontal axis indicates time and the vertical axis indicates voltage. In FIG. 31B, the horizontal axis indicates frequency and the vertical axis indicates signal intensity. The correlation coefficient of these frequency power spectrums in the transmission frequency band (3.8 MHz-18.6 MHz) at −20 dB of the ultrasound probe A is 0.827.

Comparison Example 1

First, as for the ultrasound probe 2, the ultrasound probe A the same as that in Embodiment example 1 is used.

Figure 6:
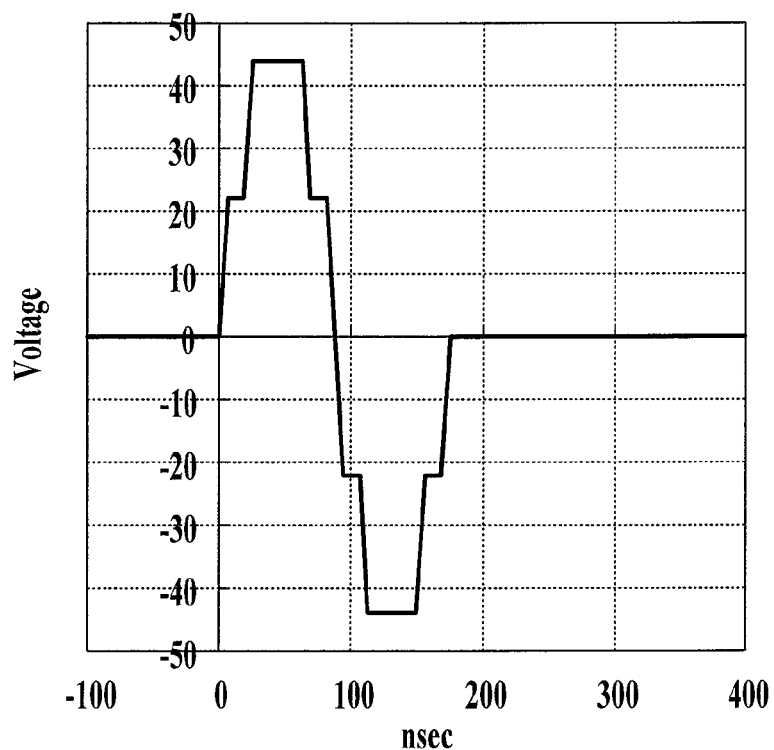
FIG. 6 is a drawing for explaining a drive waveform of a pulse signal, the drive waveform being referred to as waveform No. 1.

The first pulse signal output from the transmission unit 12 is a drive signal of waveform No. 1 as shown in FIG. 6. The drive signal of waveform No. 1 shows that the voltage starts increasing at 0 nsec, reaches +MV at 7 nsec and maintains +MV until 19 nsec (the first duty). Thereafter, the voltage starts increasing at 19 nsec, reaches +HV at 25 nsec and maintains +HV until 63 nsec (the second duty). Thereafter, the voltage starts decreasing at 63 nsec, reaches +MV at 69 nsec and maintains +MV until 82 nsec (the third duty). Thereafter, the voltage starts decreasing at 82 nsec, reaches −MV at 94 nsec and maintains −MV until 107 nsec (the fourth duty). Thereafter, the voltage starts decreasing at 107 nsec, reaches −HV at 113 nsec and maintains −HV until 150 nsec (the fifth duty). Thereafter, the voltage starts increasing at 150 nsec, reaches −MV at 157 nsec and maintains −MV until 169 nsec (the sixth duty). Thereafter, the voltage starts increasing at 169 nsec and reaches 0V at 175 nsec. In such way, the drive duration of the drive signal of waveform No. 1 is 175 nsec.

Figure 20:
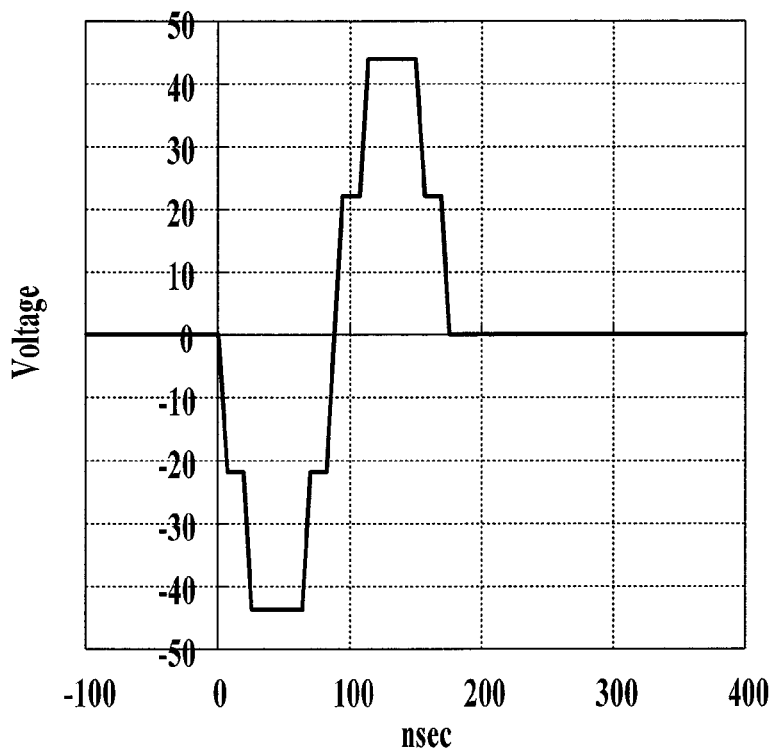
FIG. 20 is a drawing for explaining a drive waveform of a pulse signal, the drive waveform being referred to as waveform No. 15.
Figure 32A:
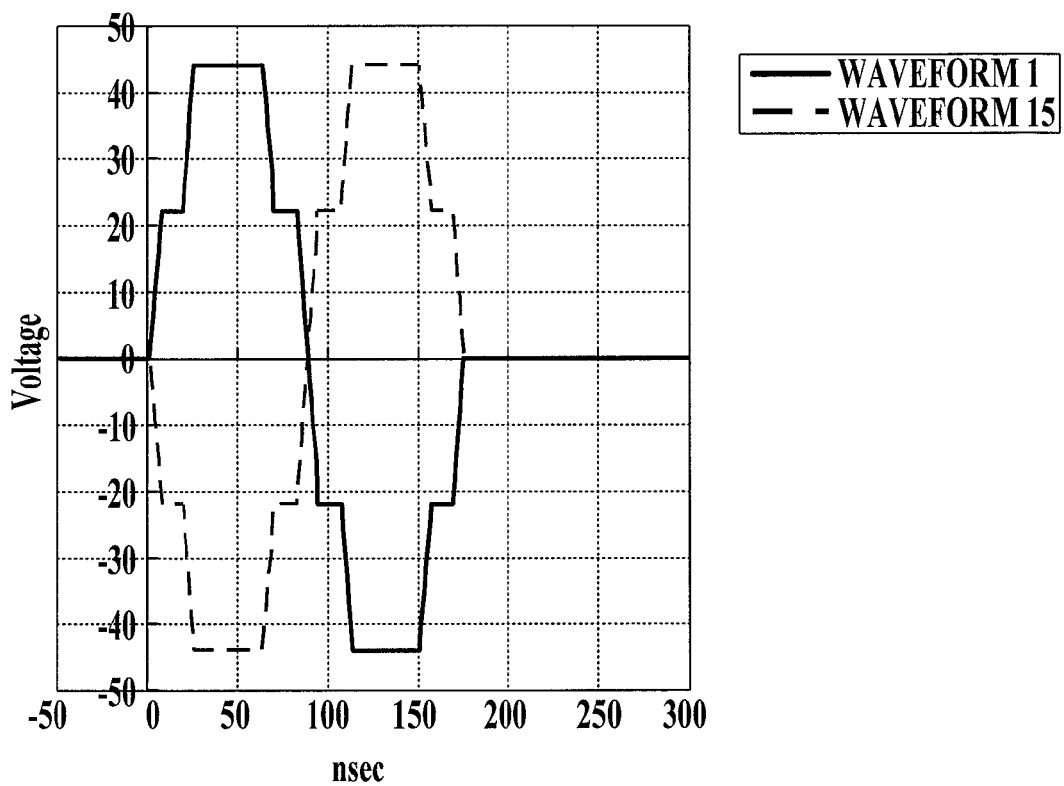
FIG. 32A is a drawing for explaining drive waveforms of pulse signals.
Figure 32B:
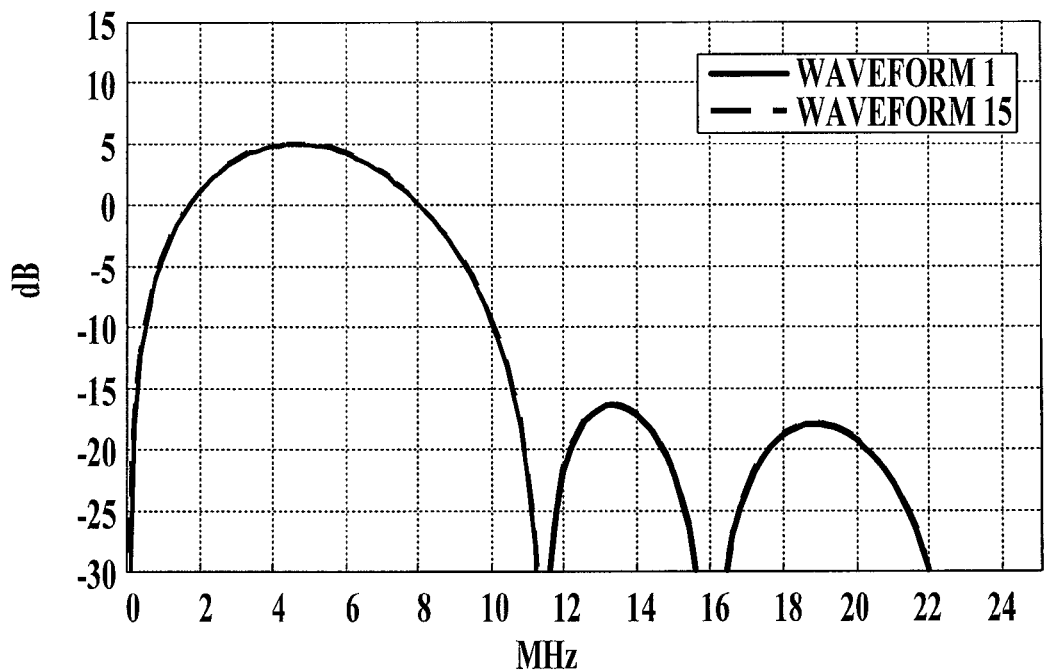
FIG. 32B is a drawing for explaining results of performing frequency analysis on the drive waveform shown in FIG. 32A.

Further, the second pulse signal is a drive signal of waveform No. 15 as shown in FIG. 20. The drive signal of waveform No. 15 shows that the voltage starts decreasing at 0 nsec, reaches −MV at 7 nsec and maintains −MV until 19 nsec (the first duty). Thereafter, the voltage starts decreasing at 19 nsec, reaches −HV at 25 nsec and maintains −HV until 63 nsec (the second duty). Thereafter, the voltage starts increasing at 63 nsec, reaches −MV at 69 nsec and maintains −MV until 82 nsec (the third duty). Thereafter, the voltage starts increasing at 82 nsec, reaches +MV at 94 nsec and maintains +MV until 107 nsec (the fourth duty). Thereafter, the voltage starts increasing at 107 nsec, reaches +HV at 113 nsec and maintains +HV until 150 nsec (the fifth duty). Thereafter, the voltage starts decreasing at 150 nsec, reaches +MV at 157 nsec and maintains +MV until 169 nsec (the sixth duty). Thereafter, the voltage starts decreasing at 169 nsec and reaches 0V at 175 nsec. In such way, the drive duration of the drive signal of waveform No. 15 is 175 nsec, the drive duration being the same as that of the drive signal of waveform No. 1. Further, as shown in FIG. 32A, the waveform of the drive signal of waveform No. 15, which is the second pulse signal, is in a shape where its positive and negative polarities are inverse of the polarities in the waveform of the drive signal of waveform No. 1, the waveform of the drive signal of waveform No. 15 being symmetric to the waveform of the drive signal of waveform No. 1. The frequency power spectrums obtained by performing frequency analysis on these drive waveforms are shown in FIG. 32B. In FIG. 32A, the horizontal axis indicates time and the vertical axis indicates voltage. In FIG. 32B, the horizontal axis indicates frequency and the vertical axis indicates signal intensity. The correlation coefficient of these frequency power spectrums in the transmission frequency band (3.8 MHz-18.6 MHz) at −20 dB of the ultrasound probe A is 1.000.

Comparison Example 2

First, as for the ultrasound probe 2, the ultrasound probe A same as that in Embodiment example 1 is used.

Figure 7:
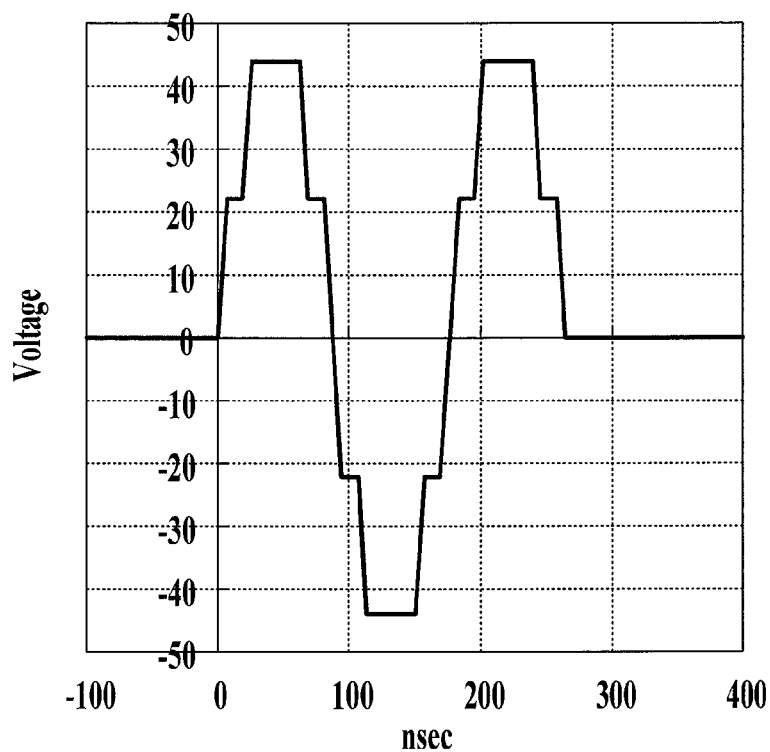
FIG. 7 is a drawing for explaining a drive waveform of a pulse signal, the drive waveform being referred to as waveform No. 2.

The first pulse signal output from the transmission unit 12 is a drive signal of waveform No. 2 as shown in FIG. 7. The drive signal of waveform No. 2 shows that the voltage starts increasing at 0 nsec, reaches +MV at 7 nsec and maintains +MV at 19 nsec (the first duty). Thereafter, the voltage starts increasing at 19 nsec, reaches +HV at 25 nsec and maintains +HV until 63 nsec (the second duty). Thereafter, the voltage starts decreasing at 63 nsec, reaches +MV at 69 nsec and maintains +MV until 82 nsec (the third duty). Thereafter, the voltage starts decreasing at 82 nsec, reaches −MV at 94 nsec and maintains −MV until 107 nsec (the fourth duty). Thereafter, the voltage starts decreasing at 107 nsec, reaches −HV at 113 nsec and maintains −MV until 150 nsec (the fifth duty). Thereafter, the voltage starts increasing at 150 nsec, reaches −MV at 157 nsec and maintains −MV until 169 nsec (the sixth duty). Thereafter, the voltage starts increasing at 169 nsec, reaches +MV at 182 nsec and maintains +MV until 194 nsec (the seventh duty). Thereafter, the voltage starts increasing at 194 nsec, reaches +HV at 200 nsec and maintains +HV until 238 nsec (the eighth duty). Thereafter, the voltage starts decreasing at 238 sec, reaches +MV at 244 nsec and maintains +MV until 257 nsec (the ninth duty). Thereafter, the voltage starts decreasing at 257 nsec and reaches 0V at 263 nsec. In such way, the drive duration of the drive signal of waveform No. 2 is 263 nsec.

Figure 21:
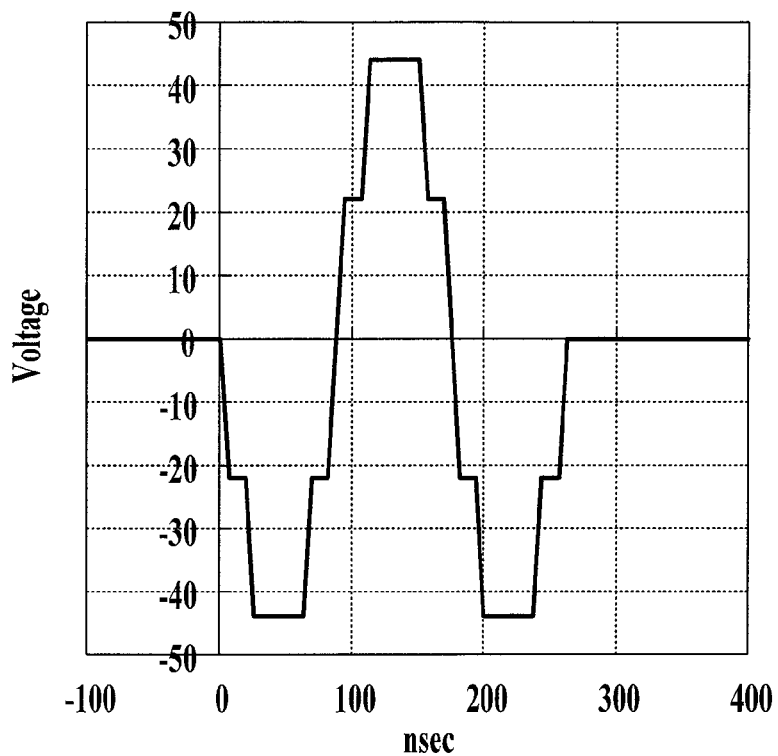
FIG. 21 is a drawing for explaining a drive waveform of a pulse signal, the drive waveform being referred to as waveform No. 16.
Figure 33A:
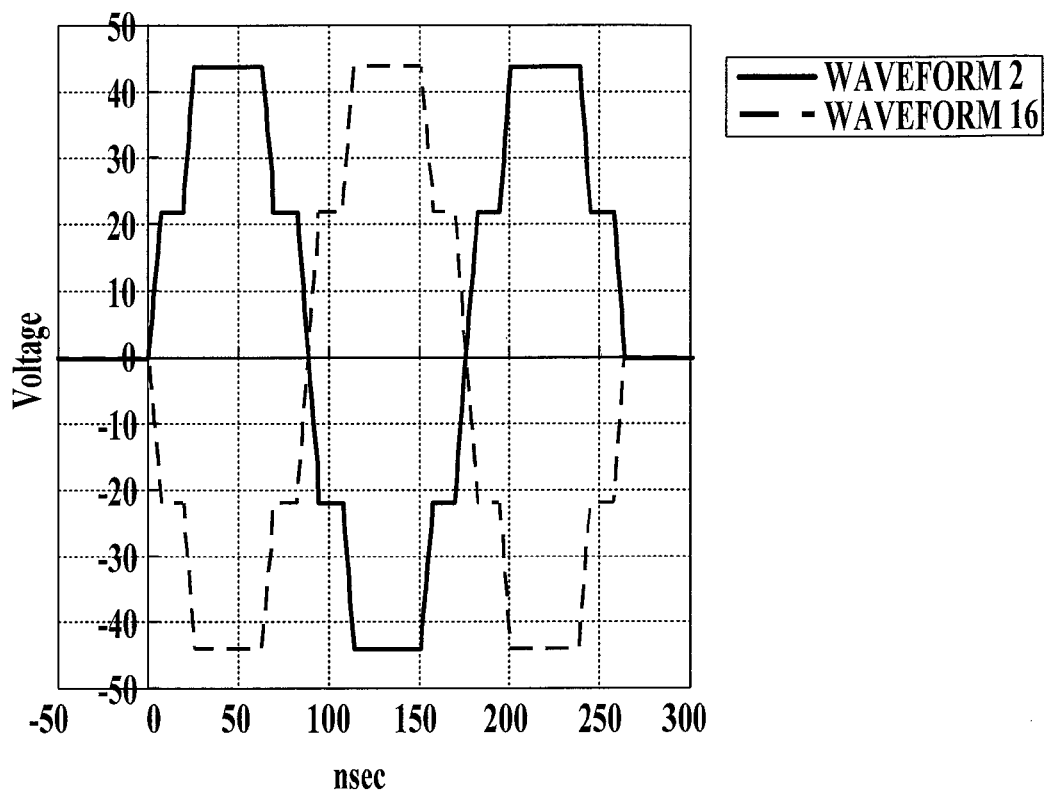
FIG. 33A is a drawing for explaining drive waveforms of pulse signals.
Figure 33B:
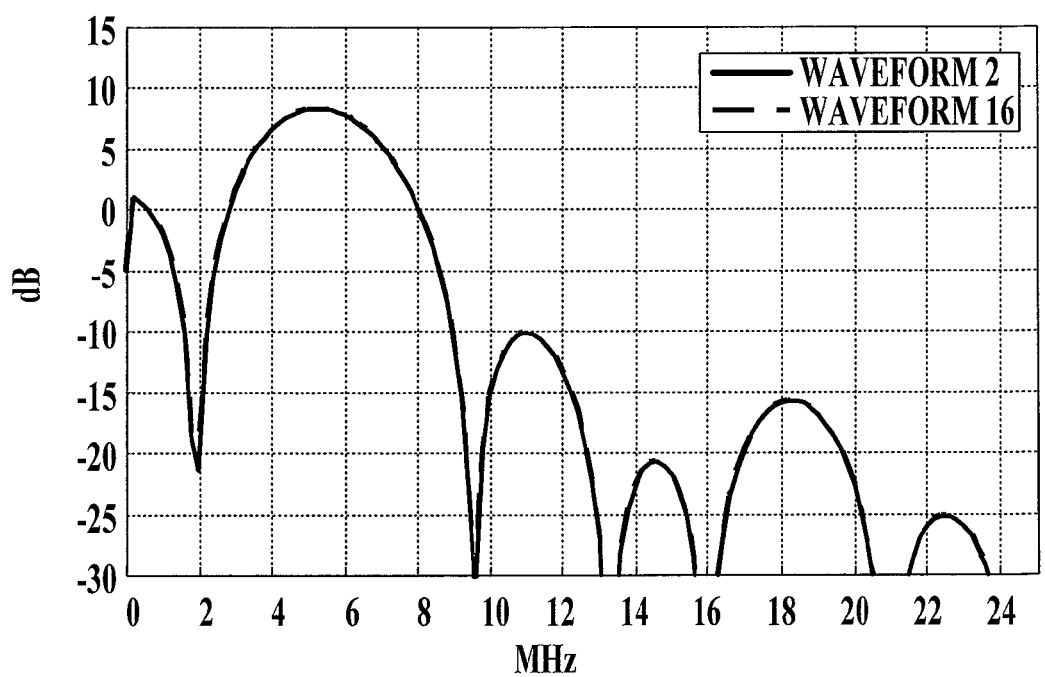
FIG. 33B is a drawing for explaining results of performing frequency analysis on the drive waveforms shown in FIG. 33A.

Further, the second pulse signal is a drive signal of waveform No. 16 as shown in FIG. 21. The drive signal of waveform No. 16 shows that the voltage starts decreasing at 0 nsec, reaches −MV at 7 nsec and maintains −MV until 19 nsec (the first duty). Thereafter, the voltage starts decreasing at 19 nsec, reaches −HV at 25 nsec and maintains −HV until 63 nsec (the second duty). Thereafter, the voltage starts increasing at 63 nsec, reaches −MV at 69 nsec and maintains −MV until 82 nsec (the third duty). Thereafter, the voltage starts increasing at 82 nsec, reaches +MV at 94 nsec and maintains +MV until 107 nsec (the fourth duty). Thereafter, the voltage starts increasing at 107 nsec, reaches −HV at 113 nsec and maintains +HV until 150 nsec (the fifth duty). Thereafter, the voltage starts decreasing at 150 nsec, reaches +MV at 157 nsec and maintains +MV until 169 nsec (the sixth duty). Thereafter, the voltage starts decreasing at 169 nsec, reaches −MV at 182 nsec and maintains −MV until 194 nsec (the seventh duty). Thereafter, the voltage starts decreasing at 194 nsec, reaches −HV at 200 nsec and maintains −HV until 238 nsec (the eighth duty). Thereafter, the voltage starts increasing at 238 nsec, reaches −MV at 244 nsec and maintains −MV until 257 nsec (the ninth duty). Thereafter, the voltage starts increasing at 257 nsec and reaches 0V at 263 nsec. In such way, the drive duration of the drive signal of waveform No. 16 is 263 nsec, the drive duration being the same at that of the drive signal of waveform No. 2. Further, as shown in FIG. 33A, the waveform of the drive signal of waveform No. 16, which is the second pulse signal, is symmetric in terms of polarity to the waveform of the drive signal of waveform No. 2. The frequency power spectrums obtained by performing frequency analysis on these drive waveforms are shown in FIG. 33B. In FIG. 33A, the horizontal axis indicates time and the vertical axis indicates voltage. In FIG. 33B, the horizontal axis indicates frequency and the vertical axis indicates signal intensity. The correlation coefficient of these frequency power spectrums in the transmission frequency band (3.8 MHz-18.6 MHz) at −20 dB of the ultrasound probe A is 1.000.

Evaluation Method

In an acoustic equivalent member same as RMI 404GS-LE0.5 manufactured by Gammex, 50 μm SUS wire is embedded at the 25 mm depth position. The first pulse signal and the second pulse signal of drive waveforms with the conditions shown in Table 1 are given to the ultrasound probe on the same scanning line with a time interval therebetween to perform transmission and reception of the first ultrasound and the second ultrasound. Then, the received signals obtained from the received first ultrasound and second ultrasound are combined by pulse inversion and an ultrasound image of THI (Tissue Harmonic Imaging) is obtained. At this time, the transmission focal point is at 25 mm. Further, the wire visualization brightness at the time of imaging is converted into acoustic intensity (dB) and 20 dB resolution (distance resolution, azimuth resolution) is obtained. Further, with respect to the acoustic equivalent member same as RMI 403GS-LE0.5 manufactured by Gammex, transmission and reception of the first ultrasound and the second ultrasound is performed with the transmission focal point at 25 mm. Further, two frames of ultrasound images are obtained as described above, correlation between these two frames of ultrasound images is obtained, depth where this correlation is smaller than 0.5 is specified and this is set as the penetration. Under their conditions in individual Embodiment examples 1 to 11 and Comparison examples 1 and 2, a distal portion of medial meniscus, superior labrum anterior and posterior and a long head of biceps brachii tendon are visualized. Then, they were evaluated based on the following evaluation criterion by the total of ten medical doctors and medical technologists who work in the fields related to orthopedics, and the values are averaged to obtain visualization scores.

Evaluation Criterion

10: visualization level excellent for recognizing the tissue condition
8: visualization level practically sufficient for recognizing the tissue condition
6: visualization level not good but at the level where the tissue condition is recognizable
4: visualization level where recognition of the tissue condition may be a problem
2: visualization level where recognition of the tissue condition is difficult These evaluation criterion are shown in the following table 1.

TABLE 1

| | | ultrasound probe | | | drive waveform | | | |
| | | | | | 1st transmission | | 2nd transmission | |
| | display mode | No. | center of bandwidth at −20 dB in transmission (MHz) | bandwidth at −20 dB in transmission (MHz-MHz) | fractional bandwidth at −20 dB in transmission | waveform No. | drive duration (nsec) | waveform No. | drive duration (nsec) |
|---|---|---|---|---|---|---|---|---|---|
| Embodiment example 1 | THI | A | 11.2 | 3.8-18.6 | 132% | 3 | 163 | 9 | 169 |
| Embodiment example 2 | | | | | | 3 | 163 | 4 | 174 |
| Embodiment example 3 | | B | 11.2 | 5.0-17.8 | 114% | | | | |
| Embodiment example 4 | | C | 11.2 | 5.6-17.3 | 104% | | | | |
| Embodiment example 5 | | A | 11.2 | 3.8-18.6 | 132% | 3 | 163 | 5 | 182 |
| Embodiment example 6 | | | | | | 3 | 163 | 6 | 188 |
| Embodiment example 7 | | | | | | 3 | 163 | 7 | 194 |
| Embodiment example 8 | | | | | | 3 | 163 | 8 | 200 |
| Embodiment example 9 | | | | | | 10 | 163 | 17 | 163 |
| Embodiment example 10 | | | | | | 13 | 125 | 14 | 125 |
| Embodiment example 11 | | | | | | 11 | 225 | 12 | 225 |
| Comparison example 1 | | | | | | 1 | 175 | 15 | 175 |
| Comparison example 2 | | | | | | 2 | 263 | 16 | 263 |

TABLE 1-continued

| | drive waveform correlation coefficient of frequency power spectrums of 1st and 2nd transmissions in bandwidth at −20 dB of probe | image quality evaluation result | | | | | |
|---|---|---|---|---|---|---|---|
| | | distance resolution (μm) | azimuth resolution (μm) | penetration (mm) | distal portion of medial meniscus | shoulder labrum acetabuli | long head of biceps brachii tendon |
| Embodiment example 1 | 0.992 | 481 | 692 | 67 | 7.3 | 7.2 | 6.8 |
| Embodiment example 2 | 0.973 | 448 | 681 | 76 | 8.3 | 7.6 | 7.3 |
| Embodiment example 3 | 0.977 | 497 | 688 | 66 | 7.2 | 7.2 | 6.5 |
| Embodiment example 4 | 0.978 | 610 | 701 | 60 | 5.8 | 6.0 | 5.0 |
| Embodiment example 5 | 0.942 | 492 | 690 | 75 | 8.0 | 7.5 | 6.7 |
| Embodiment example 6 | 0.905 | 510 | 700 | 72 | 7.6 | 7.3 | 6.5 |
| Embodiment example 7 | 0.859 | 555 | 704 | 70 | 7.2 | 7.0 | 6.1 |
| Embodiment example 8 | 0.835 | 605 | 710 | 66 | 6.9 | 6.8 | 5.3 |
| Embodiment example 9 | 0.961 | 490 | 689 | 65 | 7.1 | 7.2 | 6.6 |
| Embodiment example 10 | 0.965 | 457 | 694 | 60 | 6.4 | 6.6 | 7.1 |
| Embodiment example 11 | 0.827 | 490 | 691 | 60 | 6.2 | 6.3 | 6.5 |
| Comparison example 1 | 1.000 | 608 | 705 | 53 | 3.8 | 4.0 | 5.0 |
| Comparison example 2 | 1.000 | 806 | 671 | 61 | 5.6 | 5.9 | 3.8 |

Evaluation Results

From the results shown in Table 1, it is understood that Embodiment examples 1 to 11 exhibit good distance resolution and great penetration comparing to Comparison examples 1 and 2. Further, it is understood that Embodiment examples 1 to 11 have higher visualization scores for the distal portion of medial meniscus, superior labrum anterior and posterior and long head of biceps brachii tendon comparing to Comparison examples 1 and 2. Especially, Comparison example 1 has smaller penetration and lower visualization evaluation for the distal portion of medial meniscus and superior labrum anterior and posterior comparing to Embodiment examples 1 to 11, and Comparison example 2 has lower distance resolution and lower visualization evaluation for the long head of biceps brachii tendon comparing to Embodiment examples 1 to 11.

As described above, in the embodiment, the ultrasound probe 2 outputs transmission ultrasound toward a subject by a pulse signal being input and outputs received signals by receiving reflected ultrasound from the subject. The transmission unit 12 outputs a pulse signal of a drive waveform formed of rectangular waves to make the ultrasound probe 2 generate transmission ultrasound. The transmission unit 12 outputs pulse signals whose drive waveforms are asymmetric to each other on a same scanning line with a time interval therebetween for a plurality of times. The image generation unit 14 and the image processing unit 15 combines the received signals each of which obtained from the reflected ultrasound of the transmission ultrasound generated by each output of pulse signal to generate ultrasound image data based on the composite received signal. As a result, penetration can be improved while maintaining resolution even when a transmission drive device that realizes high positive and negative drive symmetry is not provided.

Further, according to the embodiment, the transmission unit 12 outputs the first pulse signal and the second pulse signal which is a pulse signal formed by at least one of the plurality of duties in the first pulse signal being changed and by performing time reversal or polarity reversal thereto. As a result, a remainder component which remains, not being able to control, as an unwanted component due to distortion in positive and negative symmetry in a conventional transmission unit, can be controlled to be remained as a preferable component according to this method. Therefore, image quality can be improved by a simple method.

Furthermore, according to the embodiment, the transmission unit 12 outputs a plurality of pulse signals for different drive pulse duration. Therefore, resolution and penetration can be improved by a simple method.

Moreover, according to the embodiment, the transmission unit 12 outputs the first pulse signal and the second pulse signal whose drive pulse duration is different from the drive pulse duration of the first pulse signal, the second pulse signal being formed by making the duty at the first peak among the plurality of duties in the first pulse signal be longer for a predetermined time length and performing time reversal or polarity reversal thereto. As a result, resolution and penetration can be improved by a simple method.

Further, according to the embodiment, the transmission unit 12 outputs a plurality of pulse signals so that the correlation coefficient of the pulse signals be 0.85 or greater and less than 1 in the transmission and reception bandwidth at −20 dB of the ultrasound probe 2. As a result, an ultrasound image of high image quality in which resolution and penetration are improved can be obtained.

Furthermore, according to the embodiment, the fractional bandwidth at −20 bB of the ultrasound probe 2 is 110% or greater. Therefore, ultrasound of higher resolution can be transmitted.

Moreover, according to the embodiment, since a pulse signal is formed of rectangular waves of five values or less, resolution can be improved at a low cost.

The Description of the embodiment of the present invention is merely an example of an ultrasound diagnostic imaging apparatus according to the present invention and the present invention is not limited to what is described. The detail configuration and detail operations of the functional parts which constitute the ultrasound diagnostic imaging apparatus can be modified arbitrarily.

Further, in the embodiment, with respect to the frequency power spectrums of the first pulse signal and the second pulse signal, it is preferred that the correlation coefficient thereof in the transmission frequency band at −20 dB of the ultrasound probe 2 is 0.85 or greater. However, the correlation coefficient may be smaller than 0.85.

The entire disclosure of Japanese Patent Application No. 2013-055837 filed on Mar. 19, 2013 is incorporated herein by reference in its entirety.

What is claimed is:

1. An ultrasound diagnostic imaging apparatus which uses pulse inversion, comprising:
    an ultrasound probe which outputs transmission ultrasound toward a subject due to a pulse signal being input and which outputs a received signal by receiving reflected ultrasound from the subject;
    a transmission circuit which makes the ultrasound probe generate the transmission ultrasound by outputting a pulse signal whose drive waveform is formed of rectangular waves; and
    a processor which generates ultrasound image data using pulse inversion,
    wherein the transmission circuit outputs, as the pulse signal, a first pulse signal and a second pulse signal on a same scanning line with a time interval therebetween,
    wherein a correlation coefficient of frequency components of the first pulse signal and the second pulse signal is 0.85 or greater and less than 1 in a transmission and reception bandwidth at −20 dB of the ultrasound probe,
    wherein the processor combines, by pulse inversion, a first received signal which is obtained from the reflected ultrasound of the transmission ultrasound generated by the first pulse signal and a second received signal which is obtained from the reflected ultrasound of the transmission ultrasound generated by the second pulse signal, such that harmonic components are emphasized, a majority part of fundamental wave components are canceled, and a part of the fundamental wave components which is not canceled by combining the first received signal and the second received signal remains as a remainder component, in accordance with the correlation coefficient of the frequency components of the first pulse signal and the second pulse signal; and
    wherein the processor generates the ultrasound image data using the emphasized harmonic components and the remainder component.

2. The ultrasound diagnostic imaging apparatus of claim 1, wherein the transmission circuit forms the second pulse signal by changing at least one duty among a plurality of duties in the first pulse signal and performing time reversal or polarity reversal to the first pulse signal.

3. The ultrasound diagnostic imaging apparatus of claim 1, wherein the transmission circuit changes a drive pulse duration of at least one of the first pulse signal and the second pulse signal.

4. The ultrasound diagnostic imaging apparatus of claim 1, wherein the transmission circuit outputs the first pulse signal and the second pulse signal such that a drive pulse duration of the second pulse signal is different from a drive pulse duration of the first pulse signal, and wherein the transmission circuit forms the second pulse signal by making a first duty among a plurality of duties in the first pulse signal longer for a predetermined time period and performing time reversal or polarity reversal to the first pulse signal.

5. The ultrasound diagnostic imaging apparatus of claim 1, wherein in the ultrasound probe, a fractional bandwidth at −20 dB is 110% or greater.

6. The ultrasound diagnostic imaging apparatus of claim 1, wherein the first pulse signal and the second pulse signal are formed of rectangular waves of five voltage values or less.

7. The ultrasound diagnostic imaging apparatus of claim 1, wherein drive waveforms of the first pulse signal and the second pulse signal are at least one of not line-symmetric to each other and not point-symmetric to each other.

8. The ultrasound diagnostic imaging apparatus of claim 1, wherein drive waveforms of the first pulse signal and the second pulse signal do not match even when the waveform of the second pulse signal is at least one of time reversed and polarity reversed.

9. The ultrasound diagnostic imaging apparatus of claim 1, wherein the processor extracts the emphasized harmonic components obtained by combining the first received signal and the second received signal.

* * * * *